US009534256B2

(12) United States Patent
Xu et al.

(10) Patent No.: US 9,534,256 B2
(45) Date of Patent: Jan. 3, 2017

(54) METHODS AND COMPOSITIONS FOR CORRELATING GENETIC MARKERS WITH RISK OF AGGRESSIVE PROSTATE CANCER

(75) Inventors: Jianfeng Xu, Clemmons, NC (US); William B. Isaacs, Glyndon, MD (US); Henrik Grönberg, Stockholm (SE)

(73) Assignees: Wake Forest University Health Sciences, Winston-Salem, NC (US); The Johns Hopkins University, Baltimore, MD (US)

(*) Notice: Subject to any disclaimer, the term of this patent is extended or adjusted under 35 U.S.C. 154(b) by 170 days.

(21) Appl. No.: 13/344,907

(22) Filed: Jan. 6, 2012

(65) Prior Publication Data
US 2012/0178082 A1 Jul. 12, 2012

Related U.S. Application Data

(60) Provisional application No. 61/430,352, filed on Jan. 6, 2011.

(51) Int. Cl.
*C12Q 1/68* (2006.01)
*C12P 19/34* (2006.01)

(52) U.S. Cl.
CPC ....... *C12Q 1/6886* (2013.01); *C12Q 2600/156* (2013.01)

(58) Field of Classification Search
CPC .. C12Q 1/686; C12Q 1/6872; C12Q 2600/156
See application file for complete search history.

(56) References Cited

U.S. PATENT DOCUMENTS

| | | | |
|---|---|---|---|
| 6,306,087 B1 | 10/2001 | Barnhill et al. | |
| 6,316,196 B1* | 11/2001 | Morten | 435/6.14 |
| 6,355,427 B1 | 3/2002 | Jupe et al. | |
| 6,581,038 B1 | 6/2003 | Mahran | |
| 7,127,355 B2 | 10/2006 | Cox et al. | |
| 7,718,372 B2 | 5/2010 | Cramer et al. | |
| 7,960,109 B2 | 6/2011 | Hessels et al. | |
| 7,998,674 B2 | 8/2011 | Kao et al. | |
| 2008/0038744 A1 | 2/2008 | Cramer et al. | |
| 2009/0099789 A1 | 4/2009 | Stephan et al. | |
| 2009/0226912 A1 | 9/2009 | Xu et al. | |
| 2009/0299645 A1 | 12/2009 | Colby et al. | |
| 2009/0307179 A1 | 12/2009 | Colby et al. | |
| 2009/0307181 A1 | 12/2009 | Colby et al. | |
| 2009/0317799 A1 | 12/2009 | Amundadottir et al. | |
| 2009/0324559 A1 | 12/2009 | Sakurada et al. | |
| 2010/0041037 A1 | 2/2010 | Gudmundsson et al. | |
| 2010/0042438 A1 | 2/2010 | Moore et al. | |
| 2010/0047782 A1 | 2/2010 | Cotterchio et al. | |
| 2010/0070455 A1 | 3/2010 | Halperin et al. | |
| 2010/0120045 A1 | 5/2010 | Helgadottir et al. | |
| 2010/0129799 A1 | 5/2010 | Gudmundsson et al. | |
| 2010/0130526 A1 | 5/2010 | Glinsky | |
| 2012/0150032 A1* | 6/2012 | Gudmundsson et al. | 600/437 |
| 2012/0178082 A1 | 7/2012 | Xu et al. | |
| 2014/0057795 A1 | 2/2014 | Xu et al. | |
| 2015/0031032 A1 | 1/2015 | Xu | |

FOREIGN PATENT DOCUMENTS

| | | |
|---|---|---|
| WO | WO 2006/123369 A1 | 11/2006 |
| WO | WO 2008/050356 A1 | 5/2008 |
| WO | WO 2008/096375 A2 | 8/2008 |
| WO | WO 2009/056862 A2 | 5/2009 |
| WO | WO 2009/069152 A2 | 6/2009 |
| WO | WO 2009/085196 A1 | 7/2009 |
| WO | WO 2009/117122 A2 | 9/2009 |
| WO | WO 2010/012823 A1 | 2/2010 |
| WO | WO 2012/031207 A2 | 3/2012 |
| WO | WO 2012/129408 A2 | 9/2012 |
| WO | WO 2014/152950 A1 | 9/2014 |

OTHER PUBLICATIONS ss75869428 for rs4054823, dbSNP, NCBI, NLM, 2007.*
ss74916614 for rs7215323, dbSNP, NCBI, NLM, 2007.*
Andiappan (BMC Genetics. 2010. 11: 36).*
Sotos et al. Statistics Education Research Journal Nov. 2009, 8(2):33-55.*
Terwilliger and Hiekkalinna European Journal of Human Genetics (2006) 14, 426-437.*
Langdahl (Journal of Bone and Mineral Research 2000 vol. 15, No. 3, pp. 402-414).*
Wall (Nature Reviews Genetics (2003) vol. 4, pp. 587-597).*
Xue et al; Cancer Epidemiology, Biomarkers, and Prevention, vol. 10, pp. 575-579, 2001.*
Adolfsson et al. "Clinical characteristics and primary treatment of prostate cancer in Sweden between 1996 and 2005" *Scandinavian Journal of Urology and Nephrology*, 2007; 41:456-477.
Al Olama et al. "Multiple loci on 8q24 associated with prostate cancer susceptibility" *Nature Genetics*, 2009; 41(10):1058-1060.
Amundadottir et al. "A common variant associated with prostate cancer in European and African populations" *Nature Genetics*, 2006; 39(6):652-658.
Andriole et al. "Mortality Results from a Randomized Prostate-Cancer Screening Trial" *The New England Journal of Medicine*, 2009; 360:1310-1319.
Chang et al. "Fine mapping association study and functional analysis implicate a SNP in MSMB at 10q11 as a causal variant for prostate cancer risk" *Human Molecular Genetics*, 2009; 18(7):1368-1375.
Cheng et al. "8q24 and prostate cancer: association with advanced disease and meta-analysis" *European Journal of Human Genetics*, 2008: 16:496-505.
Cooperberg et al. "Risk Assessment for Prostate Cancer Metastasis and Mortality at the Time of Diagnosis" *J Natl Cancer Inst*, 2009; 101:878-887.
Duggan et al. "Two Genome-wide Association Studies of Aggressive Prostate Cancer implicate Putative Prostate Tumor Suppressor Gene DAB2IP" *J Natl Cancer Inst*, 2007; 99:1836-1844.

(Continued)

Primary Examiner — Jehanne Sitton
(74) Attorney, Agent, or Firm — Myers Bigel, P.A.

(57) ABSTRACT

The present invention provides a method of identifying a subject as having an increased risk of having or developing aggressive prostate cancer, comprising detecting in the subject the presence of various polymorphisms associated with an increased risk of having or developing aggressive prostate cancer.

2 Claims, 2 Drawing Sheets

(56) References Cited

OTHER PUBLICATIONS

Eeles et al. "Identification of seven new prostate cancer susceptibility loci through a genome-wide association study" *Nature Genetics*, 2009; 41(10):1116-1123.

Eeles et al. "Multiple newly identified loci associated with prostate cancer susceptibility" *Nature Genetics*, 2008; 40(3):316-321.

Epstein et al. "The 2005 International Society of Urological Pathology (ISUP) Consensus Conference on Gleason Grading of Prostatic Carcinoma" *Am J Surg Pathol*, 2005; 29(9):1228-1242.

FitzGerald et al "Analysis of Recently Identified Prostate Cancer Susceptibility Loci in a Population-based Study: Associations with Family History and Clinical Features" *Clin Cancer Res*, 2009;15:3231-3237.

Freedman et al. "Admixture mapping identifies 8q24 as a prostate cancer risk locus in African-American men" *PNAS*, 2006; 103(38):14068-14073.

Gelmann et al. "Complexities of Prostate-Cancer Risk" *New England Journal of Medicine*, 2008; 358(9):961-963.

Gudmundsson et al. "Common sequence variants on 2p15 and Xp11.22 confer susceptibility to prostate cancer" *Nature Genetics*, 2008; 40(3):281-283.

Gudmundsson et al. "Genome-wide association and replication studies identify four variants associated with prostate cancer susceptibility" *Nature Genetics*, 2009; 41(10):1122-1128.

Gudmundsson et al. "Genome-wide association study identifies a second prostate cancer susceptibility variant at 8q24" *Nature Genetics*, 2007; 39(5):631-637.

Gudmundsson et al. "Two variants on chromosome 17 confer prostate cancer risk, and the one in TCF2 protects against type 2 diabetes" *Nature Genetics*, 2007; 39(8):977-983.

Haiman et al. "Multiple regions within 8q24 independently affect risk for prostate cancer" *Nature Genetics*, 2007; 39(5):638-644.

Helfand et al. "Tumor Characteristics of Carriers and Noncarriers of the decode 8q24 Prostate Cancer Susceptibility Alleles" *The Journal of Urology*, 2008; 179:2197-2202.

Hoedemaeker et al. "Staging Prostate Cancer" *Microscopy Research and Technique*, 2009; 51:423-429.

Hsu et al. "A Novel Prostate Cancer Susceptibility Locus at 19q13" *Cancer Res*, 2009; 69:2720-2723.

Hsu et al. "Comparison of two methods for estimating absolute risk of prostate cancer based on SNPs and family history" *Cancer Epidemiol Biomarkers Prev*, Apr. 2010; 19(4):1083-1088.

Jemal et al. "Cancer Statistics, 2009" *CA Cancer J Clin*, 2009; 59:225-249.

Jin et al. "Genome-wide copy-No. variation analysis identifies common genetic variants at 20p13 associated with aggressiveness of prostate cancer" *Carcinogenesis*, 2011; 32:1057-1062.

Kader et al. "Individual and cumulative Effect of Prostate Cancer Risk-Associated Variants on Clinicopathologic Variables in 5,895 Prostate Cancer Patients" *The Prostate*, 2009; 69:1195-1205.

Kim et al. "Prostate cancer risk-associated variants reported from genome-wide association studies: meta-analysis and their contribution to genetic variation" *Prostate*, 2010; 70(16):1729-1738.

Kote-Jarai et al. "Multiple Novel Prostate Cancer Predisposition Loci Confirmed by an International Study: The Practical Consortium" *Cancer Epidemiol Biomarkers Prev*, 2008;17:2052-2061.

Kraft et al. "Genetic Risk Prediction—Are We There Yet?" *The New England Journal of Medicine*, 2009; 360(17)1701-1703.

Lin. "Functions of heparin sulfate proteoglycans in cell signaling during development" *Development*, 2004;131:6009-6021.

Lindström et al. "Familial concordance in cancer survival: a Swedish population-based study" *Lancet Oncol*, 2007; 8:1001-06.

Lotan et al. "Gleason grading of prostatic adenocarcinoma with glomeruloid features on needle biopsy" *Human Pathology*, 2009; 40:471-477.

Schaid et al. "Pooled genome linkage scan of aggressive prostate cancer: Results from the International Consortium for Prostate Cancer Genetics" *Hum Genet*, 2006; 120:471-485.

Schröder et al. "Screening and Prostate-Cancer Mortality in a Randomized European Study" *The New England Journal of Medicine*, 2009; 360:13:1320-1328.

Stattin et al. "Surveillance and Deferred Treatment for Localized Prostate Cancer. Population Based Study in the National Prostate Cancer Register of Sweden" *The Journal of Urology*, 2008; 180:2423-2430.

Stephenson et al. "Prostate Cancer-Specific Mortality After Radical Prostatectomy for Patients Treated in the Prostate-Specific Antigen Era" *J Clin Oncol*, 2009: 27:4300-4305.

Sun et al. "Evidence for two independent prostate cancer risk-associated loci in the HNF1B gene at 17q12" *Nature Genetics*, 2008; 40(10):1153-1155.

Sun et al. "Sequence Variants at 22q13 Are Associated with Prostate Cancer Risk" *Cancer Res*, 2009; 69:10-15.

Sun et al. "Inherited genetic markers discovered to date are able to identify a significant number of men at considerably elevated risk for prostate cancer" *Prostate*, online publication Sep. 28, 2010; 71(4):421-430.

Thomas et al. "Multiple loci identified in a genome-wide association study of prostate cancer" *Nature Genetics*, 2008; 40(3):310-315.

Wiklund et al. "Established Prostate Cancer Susceptibility Variants are not Associated with Disease Outcome" *Cancer Epidemiol Biomarkers Prev*, 2009; 18:1659-1662.

Witte et al. "Prostate cancer genomics: towards a new understanding" *Nature Reviews Genetics*, 2009; 10:77-82.

Xu et al. "Estimation of Absolute Risk for Prostate Cancer using Genetic Markers and Family History" *Prostate*, 2009; 69(14):1565-1572.

Xu et al. "Inherited genetic variant predisposes to aggressive but not indolent prostate cancer" *PNAS*, online publication Jan. 11, 2010; 107(5):2136-2140.

Yeager et al. "Genome-wide association study of prostate cancer identifies a second risk locus at 8q24" *Nature Genetics*, 2007; 39(5):645-649.

Yeager et al. "Identification of a new prostate cancer susceptibility locus on chromosome 8q24" *Nature Genetics*, 2009; 41(10):1055-1057.

Zheng et al. "Association Between Two Unlinked Loci at 8q24 and Prostate Cancer Risk Among European Americans" *J Natl Cancer Inst.*, 2007; 99:1525-33.

Zheng et al. "Cumulative Association of Five Genetic Variants with Prostate Cancer" *The New England Journal of Medicine*, 2008; 358(9):910-919.

Zheng et al. "Two Independent Prostate Cancer Risk-Associated Loci at 11q13" *Cancer Epidemiol Biomarkers Prev.*, 2009; 18:1815-1820.

Chae et al. "Genetic Polymorphisms of Estrogen Receptors α and β and the Risk of Developing Prostate Cancer" *PloS ONE* 4(8):e6523 (2009).

Chang et al. "Integration of Somatic Deletion Analysis of Prostate Cancers and Germline Linkage Analysis of Prostate Cancer Families Reveals Two Small Consensus Regions for Prostate Cancer Genes at 8p" *Cancer Res.* 67 9 :4098-4103 (2007).

Chang et al. "Two-Locus Genome-Wide Linkage Scan for Prostate Cancer Susceptibility Genes With an Interaction Effect" *Hum. Genet.* 118:716-724 (2006).

Cheng et al, "Genetic and Epigenetic Inactivation of *TNFRSF10C* in Human Prostate Cancer" *The Prostate* 69:327-335 (2009).

Dianat et al. "Gene Polymorphisms and Prostate Cancer: the Evidence" *Journal Compilation* 104:1560-1572 (2009).

Grönberg. "Prostate Cancer Epidemiology" *The Lancet* 361:859-864 (2003).

Hsu et al. "A Multigenic Approach to Evaluating Prostate Cancer Risk in a Systematic Replication Study" *Cancer Genetics and Cytogenetics* 183:94-98 (2008).

Hsu et al. "A Novel Prostate Cancer Susceptibility Locus at 19q13" *Cancer Res* 69(7):2720-2723 (2009).

Hunter and Kraft. "Drinking From the Fire Hose—Statistical Issues in Genomewide Association Studies" *N. Engl. J. Med.* 357(5):436-439 (2007).

(56) References Cited

OTHER PUBLICATIONS

International Preliminary Report on Patentability Corresponding to International Application No. PCT/US2011/050337; Date of Mailing: Mar. 14, 2013 (7 pages).
International Search Report and Written Opinion for International Application No. PCT/US2011/050337, mailed Apr. 26, 2012 (12 pages).
International Search Report and Written Opinion of International Application No. PCT/US08/13874, mailed Apr. 14, 2009 (13 pages).
Jemal et al. "Cancer Statistics, 2007" *CA Cancer J. Clin.* 57(1):43-66 (2007).
Johns and Houlston. "A Systematic Review and Meta-Analysis of Familial Prostate Cancer Risk" *BJU International* 91:789-794 (2003).
Kim et al. "Genetic and Epigenetic Inactivation of *LPL* Gene in Human Prostate Cancer" *Int. J. Cancer* 124:734-738 (2009).
Lange et al. "Family-Based Samples Can Play an Important Role in Genetic Association Studies" *Cancer Epidemiol Biomarkers Prev* 17(9):2208-2214 (2008).
Lange et al. "Fine-Mapping the Putative Chromosome 17q21-22 Prostate Cancer Susceptibility Gene to a 10 cM Region Based on Linkage Analysis" *Hum. Genet.* 121:49-55 (2007).
Levin et al. "Chromosome 17q12 Variants Contribute to Risk of Early-Onset Prostate Cancer" *Cancer Res* 68(16):6492-6495 (2008).
Lindmark et al. "Interleukin-1 Receptor Antagonist Haplotype Associated With Prostate Cancer Risk" *British Journal of Cancer* 93:493-497 (2005).
Lindström et al. "Comprehensive Genetic Evaluation of Common E-Cadherin Sequence Variants and Prostate Cancer Risk: Strong Confirmation of Functional Promoter SNP" *Hum. Genet.* 118:339-347 (2005).
Lindström et al. "Germ-Line Genetic Variation in the Key Androgen-Regulating Genes *Androgen Receptor, Cytochrome P450*, and *Steriod-5-α-Reductase Type 2* is Important for Prostate Cancer Development" *Cancer Res.* 66(22):11077-11083 (2006).
Lindström et al. "Systematic Replication Study of Reported Genetic Associations in Prostate Cancer: Strong Support for Genetic Variation in the Androgen Pathway" *The Prostate* 66:1729-1743 (2006).
Liu et al. "Association of a Germ-Line Copy Number Variation at 2p24.3 and Risk for Aggressive Prostate Cancer" *Cancer Res* 69(6):2176-2179 (2009).
Liu et al. "Comprehensive Assessment of DNA Copy Number Alterations in Human Prostate Cancers Using Affymetrix 100K SNP Mapping Array" *Genes, Chromosomes & Cancer* 45:1018-1032 (2006).
Liu et al. "Deletion of a Small Consensus Region at 6q15, Including the *MAP3K7* Gene, is Significantly Associated with High-Grade Prostate Cancers" *Human Cancer Biology* 13(17):5028-5033 (2007).
Liu et al. "Germline Copy Number Polymorphisms Involving Larger Than 100 kb Are Uncommon in Normal Subjects" *The Prostate* 67:227-233 (2007).
Liu et al. "Homozygous Deletions and Recurrent Amplifications Implicate New Genes Involved in Prostate Cancer" *Neoplasia* 10(8):897-907 (2008).
Liu et al. "Multiple Genomic Alterations on 21q22 Predict Various *TMPRSS2/ERG* Fusion Transcripts in Human Prostate Cancers" *Genes, Chromosomes & Cancer* 46:972-980 (2007).
Robbins et al. "Confirmation Study of Prostate Cancer Risk Variants at 8q24 in African Americans Identifies a Novel Risk Locus" *Genome Research* 17:1717-1722 (2007).
Schumacher et al. "A Common 8q24 Variant in Prostate and Breast Cancer From a Large Nested Case-Control Study" *Cancer Res.* 67(7):2951-2956 (2007).
Severi et al. "The Common Variant rs1447295 on Chromosome 8q24 and Prostate Cancer Risk: Results From an Australian Population-Based Case-Control Study" *Cancer Epidemiol. Biomarkers Prev.* 16(3):610-612 (2007).
Sobti et al. "Role of Hormonal Genes and Risk of Prostate Cancer: Gene-Gene Interactions in a North Indian Population" *Cancer Genetics and Cytogenetics* 185:78-85 (2008).
Sun et al. "Association Between Sequence Variants at 17q12 and 17q24.3 and Prostate Cancer Risk in European and African Americans" *The Prostate* 68:691-697 (2008).
Sun et al. "Chromosome 8q24 Risk Variants in Hereditary and Non-Hereditary Prostate Cancer Patients" *The Prostate* 68:489-497 (2008).
Sun et al. "Cumulative Effect of Five Genetic Variants on Prostate Cancer Risk in Multiple Study Populations" *The Prostate* 68:1257-1262 (2008).
Sun et al. "DNA Copy Number Alterations in Prostate Cancers: A Combined Analysis of Published CGH Studies" *The Prostate* 67:692-700 (2007).
Sun et al. "Interactions of Sequence Variants in *Interleukin-1 Receptor-Associated Kinase4* and the *Toll-Like Receptor 6-1-10* Gene Cluster Increase Prostate Cancer Risk" *Cancer Epidemiol. Biomarkers Prev.* 15(3):480-485 (2006).
Sun et al. "Meta-Analysis of Association of Rare Mutations and Common Sequence Variants in the *MSR1* Gene and Prostate Cancer Risk" *The Prostate* 66:728-737 (2006).
Sun et al. "Sequence Variants at 22q13 Are Associated With Prostate Cancer Risk" *Cancer Res* 69(1):10-15 (2009).
Suuriniemi et al. "Confirmation of a Positive Association Between Prostate Cancer Risk and a Locus at Chromosome 8q24" *Cancer Epidemiol. Biomarkers Prev.* 16(4):809-814 (2007).
Wang et al. "Two Common Chromosome 8q24 Variants Are Associated With Increased Risk for Prostate Cancer" *Cancer Res* 67(7):2944-2950 (2007).
Wiklund et al. "Association of Reported Prostate Cancer Risk Alleles With PSA Levels Among Men Without a Diagnosis of Prostate Cancer" *The Prostate* 69:419-427 (2009).
Witte "Multiple prostate cancer risk variants on 8q24", *Nature Genetics*, vol. 39, No. 5, 579-580, May 2007.
Xu et al. "Association of Prostate Cancer Risk Variants With Clinicopathologic Characteristics of the Disease" *Clin Cancer Res* 14(18):5819-5824 (2008).
Xu et al. "Germline *ATBF1* Mutations and Prostate Cancer Risk" *The Prostate* 66:1082-1085 (2006).
Xu et al. "The Interaction of Four Genes in the Inflammation Pathway Significantly Predicts Prostate Cancer Risk" *Cancer Epidemiol. Biomarkers Prev.* 14(11):2563-2568 (2005).
Zabaleta et al. "Interactions of Cytokine Gene Polymorphisms in Prostate Cancer Risk" *Carcinogenesis* 29(3):573-578 (2008).
Zheng et al. "A Comprehensive Association Study for Genes in Inflammation Pathway Provides Support for Their Roles in Prostate Cancer Risk in the CAPS Study" *The Prostate* 66:1556-1564 (2006).
Zheng et al. "Cumulative Association of Five Genetic Variants with Prostate Cancer" *N. Engl. J. Med.* 358(9):910-919 (2008); including related correspondence and authors' reply 358(25):2738-2741 (2008).
Zheng et al. "Genetic Variants and Family History Predict Prostate Cancer Similar to Prostate-Specific Antigen" *Clin Cancer Res* 15(3):1105-1111 (2009).
Zheng et al. "Germ-Line Mutation of *NKX3.1* Cosegregates with Hereditary Prostate Cancer and Alters the Homeodomain Structure and Function" *Cancer Res.* 66(1):69-77 (2006).
Zheng et al. "Two Independent Prostate Cancer Risk-Associated Loci at 11q13" *Cancer Epidemiol Biomarkers Prev* 18(6):1815-1820 (2009).
Kader et al. "Potential Impact of Adding Genetic Markers to Clinical Parameters in Predicting Prostate Biopsy Outcomes in Men Following an Initial Negative Biopsy: Findings from the Reduce Trial" *European Urology* 62(6):953-961 (2012).
Liu et al. "Genetic Markers Associated With Early Cancer-Specific Mortality Following Prostatectomy" *Cancer* 119(13):2405-2412 (2013).
Lu et al, "Association of prostate cancer risk with SNPs in regions containing androgen receptor binding sites captures by ChIP-on-chip analyses" *The Prostate* 72(4):376-385 (2012).

(56) References Cited

OTHER PUBLICATIONS

Newcombe et al. "A Comparison of Bayesian and Frequentist Approaches to Incorporating External Information for the Prediction of Prostate Cancer Risk" *Genetic Epidemiology* 36(1):71-83 (2012).
Sun et al. "Clinical utility of inherited markers in determining need for repeat biopsy: results from placebo arm of the REDUCE® study" Abstract submitted for ASHG Meeting held in Washington, DC on Nov. 2-6, 2010 (1 page).
Turner et al. "Utility of Genome-Wide Association Study findings: prostate cancer as a translational research paradigm" *Journal of Internal Medicine* 271(4):344-352 (2012).
Cao et al. "MicroRNA-101 negatively regulates Ezh2 and its expression is modulated by androgen receptor and HIF-1α/HIF-1β" *Molecular Cancer* 9(108):1-12 (2010).
Christensen et al. "Genome-Wide Linkage Analysis of 1,233 Prostate Cancer Pedigrees From the International Consortium for Prostate Cancer Genetics Using Novel sumLINK and sumLOD Analyses" *The Prostate* 70:735-744 (2010).
Al Olama et al. "A meta-analysis of genome-wide association studies to identify prostate cancer susceptibility loci associated with aggressive and non-aggressive disease" *Human Molecular Genetics* 22(2):408-415 (2013).
Prokunina-Olsson et al. "Refining the Prostate Cancer Genetic Association within the *JAZF1* Gene on Chromosome 7p15.2" *Cancer Epidemiology, Biomarkers & Prevention* 19(5):1349-1355 (2010).
Xie et al. "Germ-line sequence variants of *PTEN* do not have an important role in hereditary and non-hereditary prostate cancer susceptibility" *Journal of Human Genetics* 56(7):496-502 (2011).
Kim et at "Integrative Analysis of Genomic Aberrations Associated with Prostate Cancer Prosression" *Cancer Research* 67:8229-8239 (2007).
Knowles "Role of FGFR3 in urothelial cell carcinoma: biomarker and potential therapeutic target" *World Journal of Urology* 25:581-593 (2007).
Liu et al. "Somatic DNA copy number alterations and their potential clinical utility for predicting lethal prostate cancer" *Asian Journal of Andrology* 15:586-587 (2013).
Zafarana et at "Copy Number Alterations of c-MYC and PTEN are Prognostic Factors for Relapse After Prostate Cancer Radiotherapy" *Cancer* 118:4053-4062 (2012).
International Search Report Corresponding to International Application No. PCT/US2014/028371; Date of Mailing: Jul. 22, 2014 (15 pages).
Aly et al. "Polygenic Risk Score Improves Prostate Cancer Risk Prediction: Results from the Stockholm-1 Cohort Study" *European Urology* 60:21-28 (2011).
Chang et al. "Genome-Wide Screen for Prostate Cancer Susceptibility Genes in Men With Clinically Significant Disease" *The Prostate* 64:356-361 (2005).
Ippolito et al. "An integrated functional genomics and metabolomics approach for defining poor prognosis in human neuroendocrine cancers" *PNAS* 102(28):9901-9906 (2005).
Lu et al. "Chromosomes 4 and 8 Implicated in a Genome Wide SNP Linkage Scan of 762 Prostate Cancer Families Collected by the ICPCG" *Prostate* 72(4):410-426 (2012).
Peltonen et al. "Dissecting Human Disease in the Postgenomic Era" *Science* 291:1224-1228 (2001).
"Prostate Cancer in Men with Very Low PSA", p. 12 in *Prostate Cancer Discovery, The Brady Urological Institute, Johns Hopkins Medicine* vol. 2:1-20 (2005).
Mitka, Mike "Is PSA Testing Still Useful?" *JAMA* 292(19):2326-2327 (2004).
European Patent Office Communication pursuant to Rules 70(2) and 70a(2) EPC corresponding to European Patent Application No. 11822720.6:7 pages (Jan. 9, 2014).
International Preliminary Report on Patentability corresponding to International Application No. PCT/US2008/013874:9 pages (mailed Jul. 1, 2010).

Ahn et al. "Variation in *KLK* genes, prostate-specific antigen and risk of prostate cancer" *Nature Genetics* 40(9):1032-1034 (2008).
Andriole et al. "Effect of Dutasteride on the Risk of Prostate Cancer" *The New England Journal of Medicine* 362(13):1192-1202 (2010).
Ankerst et al. "Predicting Prostate Cancer Risk Through Incorporation of Prostate Cancer Gene 3" *The Journal of Urology* 180:1303-1308 (2008).
Ankerst et al. "Evaluating the PCPT risk calculator in ten international biopsy cohorts: results from the Prostate Biopsy Collaborative Group" *World Journal of Urology* 30:181-187 (2012).
Björk et al. "Comparison of Analysis of the Different Prostate-Specific Antigen Forms in Serum for Detection of Clinically Localized Prostate Cancer" *Urology* 48:882-888 (1996).
Brawley, Otis W. "Trends in Prostate Cancer in the United States" *Journal of the National Cancer Institute Monographs* 45:152-156 (2012).
Bussemakers et al. "DD3: A New Prostate-specific Gene, Highly Overexpressed in Prostate Cancer" *Cancer Research* 59:5975-5979 (1999).
Catalona et al. "Use of the Percentage of Free Prostate-Specific Antigen to Enhance Differentiation of Prostate Cancer From Benign Prostatic Disease" *Journal of the American Medical Association* 279(19):1542-1547 (1998).
Christensson et al. "Enzymatic activity of prostate-specific antigen and its reactions with extracellular serine proteinase inhibitors" *European Journal of Biochemistry* 194:755-763 (1990).
Cullen et al. "The burden of prostate cancer in Asian nations" *Journal of Carcinogenesis* 11(7):61-69 (2012).
De Kok et al. "$DD3^{PCA3}$, a Very Sensitive and Specific Marker to Detect Prostate Tumors" *Cancer Research* 62:2695-2698 (2002).
Delong et al. "Comparing the Areas Under Two or More Correlated Receiver Operating Characteristic Curves: A Nonparametric Approach" *Biometrics* 44:837-845 (1988).
Deras et al. "PCA3: A Molecular Urine Assay for Predicting Prostate Biopsy Outcome" *The Journal of Urology* 179:1587-1592 (2008).
Djavan et al. "Optimal Predictors of Prostate Cancer on Repeat Prostate Biopsy: A Prospective Study of 1,051 Men" *The Journal of Urology* 163:1144-1149 (2000).
Easton et al. "Genome-wide association studies in cancer" *Human Molecular Genetics* 17(2):R109-R115 (2008).
Ferlay et al. "Estimates of worldwide burden of cancer in 2008: GLOBOCAN 2008" *International Journal of Cancer* 127:2893-2917 (2010).
Filella et al. "Evaluation of [-2] proPSA and Prostate Health Index (phi) for the detection of prostate cancer: a systematic review and meta-analysis" *Clinical Chemistry and Laboratory Medicine* 51(4):729-739 (2013).
Groskopf et al. "APTIMA PCA3 Molecular Urine Test: Development of a Method to Aid in the Diagnosis of Prostate Cancer" *Clinical Chemistry* 52(6):1089-1095 (2006).
International Search Report and the Written Opinion of the International Searching Authority corresponding to International Application No. PCT/US2015/055558 (13 pages) (mailed Dec. 21, 2015).
Jemal et al. "Global Cancer Statistics" *CA: A Cancer Journal for Clinicians* 61:69-90 (2011).
Jiang et al. "Prediction of Prostate Cancer From Prostate Biopsy in Chinese Men Using a Genetic Score Derived From 24 Prostate Cancer Risk-Associated SNPs" *Prostate* 73(15):1651-1659 (2013).
Karlsson et al. "A Population-based Assessment of Germline *HOXB13* G84E Mutation and Prostate Cancer Risk" *European Urology* 65:169-176 (2014).
Kattan et al. "A Preoperative Nomogram for Disease Recurrence Following Radical Prostatectomy for Prostate Cancer" *Journal of the National Cancer Institute* 90(10):766-771 (1998).
Leyten et al. "Prospective Multicentre Evaluation of *PCA3* and *TMPRSS2-ERG* Gene Fusions as Diagnostic and Prognostic Urinary Biomarkers for Prostate Cancer" *European Urology* 65:534-542 (2014).

(56) References Cited

OTHER PUBLICATIONS

Lichtenstein et al. "Environmental and Heritable Factors in the Causation of Cancer: Analyses of Cohorts of Twins from Sweden, Denmark, and Finland" *The New England Journal of Medicine* 343(2):78-85 (2000).
Loeb et al. "Prospective, Multi-Center Evaluation of the Beckman Coulter Prostate Health Index Using WHO Calibration" *The Journal of Urology* 189(5):1702-1706 (2013).
Luderer et al. "Measurement of the Proportion of Free to Total Prostate-Specific Antigen Improves Diagnostic Performance of Prostate-Specific Antigen in the Diagnostic Gray Zone of Total Prostate-Specific Antigen" *Urology* 46(2):187-194 (1995).
Marks et al. "PCA3 Molecular Urine Assay for Prostate Cancer in Men Undergoing Repeat Biopsy" *Urology* 69(3):532-535 (2007).
Nam et al. "A genome-wide association screen identifies regions on chromosomes 1q25 and 7p21 as risk loci for sporadic prostate cancer" *Prostate Cancer and Prostatic Diseases* 11:241-246 (2008).
Nassir et al. "An ancestry informative marker set for determining continental origin: validation and extension using human genome diversity panels" *BMC Genetics* 10(39):1-13 (2009).
Pencina et al. "Evaluating the added predictive ability of a new marker: From area under the ROC curve to reclassification and beyond" *Statistics in Medicine* 27:157-172 (2008).
Presti, Joseph C. "Repeat prostate biopsy—when, where, and how" *Urologic Oncology: Seminars and Original Investigations* 27:312-314 (2009).
Prestigiacomo et al. "A Comparison of the Free Fraction of Serum Prostate Specific Antigen in Men with Benign and Cancerous Prostates: The Best Case Scenario" *The Journal of Urology* 156:350-354 (1996).
Price et al. "Principal components analysis corrects for stratification in genome-wide association studies" *Nature Genetics* 38(8):904-909 (2006).
Ren et al. "Plateau Effect of Prostate Cancer Risk-Associated SNPs in Discriminating Prostate Biopsy Outcomes" *Prostate* 73(16):1824-1835 (2013).
Rosario et al. "Short term outcomes of prostate biopsy in men tested for cancer by prostate specific antigen: prospective evaluation within ProtecT study" *British Medical Journal* 344:1-12 (2012).
Salami et al. "Combining Urinary Detection of TMPRSS2:ERG and PCA3 with Serum PSA to Predict Diagnosis of Prostate Cancer" *Urologic Oncology* 31(5):566-571 (2013).
Salinas et al. "Clinical Utility of Five Genetic Variants for Predicting Prostate Cancer Risk and Mortality" *Prostate* 69(4):363-372 (2009).
Sokoll et al. "Proenzyme PSA for the Early Detection of Prostate Cancer in the 2.5-4.0 ng/mL Total PSA Range: Preliminary Analysis" *Urology* 61:274-276 (2003).
Sokoll et al. "A multicenter evaluation of the PCA3 molecular urine test: Pre-analytical effects, analytical performance, and diagnostic accuracy" *Clinica Chimica Acta* 389:1-6 (2008).
Sun et al. "Genetic Score Is an Objective and Better Measurement of Inherited Risk of Prostate Cancer than Family History" *European Urology* 63(3):585-587 (2013).
Thompson et al. "Assessing Prostate Cancer Risk: Results from the Prostate Cancer Prevention Trial" *Journal of the National Cancer Institute* 98(8):529-534 (2006).
Thompson et al. "The Performance of Prostate Specific Antigen for Predicting Prostate Cancer is Maintained After a Prior Negative Prostate Biopsy" *The Journal of Urology* 180:544-547 (2008).
Tomlins et al. "Urine *TMPRSS2:ERG* Fusion Transcript Stratifies Prostate Cancer Risk in Men with Elevated Serum PSA" *Science Translational Medicine* 3(94):1-12 (2011).
Van Gils et al. "The Time-Resolved Fluorescence-Based PCA3 Test on Urinary Sediments after Digital Rectal Examination; a Dutch Multicenter Validation of the Diagnostic Performance" *Clinical Cancer Research* 13(3):939-943 (2007).
Vickers et al. "Decision curve analysis: a novel method for evaluating prediction models" *Medical Decision Making* 26(6):565-574 (2006).
Wacholder et al. "Performance of Common Genetic Variants in Breast-Cancer Risk Models" *The New England Journal of Medicine* 362(11):986-993 (2010).
Waters et al. "Generalizability of Associations from Prostate Cancer GWAS in Multiple Populations" *Cancer Epidemiology, Biomarkers & Prevention* 18(4):1285-1289 (2009).
Xu et al. "Prostate cancer risk-associated genetic markers and their potential clinical utility" *Asian Journal of Andrology* 15:314-322 (2013).
Yanke et al. "Validation of a Nomogram for Predicting Positive Repeat Biopsy for Prostate Cancer" *The Journal of Urology* 173:421-424 (2005).
Gsur et al. "Polymorphic CAG repeats in the androgen receptor gene, prostate-specific antigen polymorphism and prostate cancer risk" *Carcinogenesis* 23(10):1647-1651 (2002).
Chen et al. "A Genetic Risk Score Combining Ten Psoriasis Risk Loci Improves Disease Prediction" *PLoS ONE* 6(4):e19454 (2011).
Karlson et al. "Cumulative Association of Twenty-Two Genetic Variants with Seropositive Rheumatoid Arthritis Risk" *Annals of the Rheumatic Diseases* 69(6):1077-1085 (2010).
Liyanarachchi et al. "Cumulative Risk Impact of Five Genetic Variants Associated with Papillary Thyroid Carcinoma" *Thyroid* 23(12):1532-1540 (2013).
Manolio, Teri A. "Cohort studies and the genetics of complex disease" *Nature Genetics* 41(1):5-6 (2009).
Park et al. "Potential Usefulness of Single Nucleotide Polymorphisms to Identify Persons at High Cancer Risk: An Evaluation of Seven Common Cancers" *Journal of Clinical Oncology* 30(17):2157-2162 (2012).
Pharoah et al. "Polygenic susceptibility to breast cancer and implications for prevention" *Nature Genetics* 31:33-36 (2002).
Pharoah et al. "Polygenes, Risk Prediction, and Targeted Prevention of Breast Cancer" *The New England Journal of Medicine* 358(26):2796-2803 (2008).
Xu, Jianfeng "Public Health Genomics: Genomic-targeted cancer screening" *Presentation at the Shanghai Forum* (May 25, 2014); *Presentation at the International Conference on Frontiers in Chronic Disease Research and Prevention* (May 31, 2014) (23 pages).
Farkas et al. "National Trends in the Epidemiology of Prostate Cancer, 1973 to 1994: Evidence for the Effectiveness of Prostate-Specific Antigen Screening" *Urology* 52(3):444-448 (1998).

\* cited by examiner

US 9,534,256 B2

METHODS AND COMPOSITIONS FOR CORRELATING GENETIC MARKERS WITH RISK OF AGGRESSIVE PROSTATE CANCER

STATEMENT OF PRIORITY

This application claims the benefit, under 35 U.S.C. §119(e), of U.S. Provisional Application Ser. No. 61/430,352, filed Jan. 6, 2011, the entire contents of which are incorporated by reference herein.

STATEMENT OF GOVERNMENT SUPPORT

This invention was made with government support under Grant Nos. CA129684, CA106523, CA105055, CA95052, CA1125117, CA133009 and CA131338 awarded by the National Institutes of Health and Grant Nos. PC051264 and W81XWH-09-1-0488 awarded by the Department of Defense. The government has certain rights in the invention.

FIELD OF THE INVENTION

The present invention provides methods and compositions directed to identification of genetic markers associated with prostate cancer.

BACKGROUND OF THE INVENTION

Prostate cancer accounts for one-fourth of all cancer diagnoses in men in the United States, with an estimated 192,280 new cases in 2009 (1). Although most men will have an indolent form of the disease, aggressive prostate cancers are currently the second leading cause of cancer deaths in men in the United States. Most cases of prostate cancer are diagnosed as a result of having an elevated serum level of prostate-specific antigen (PSA). PSA-based disease screening leading to early detection and treatment of prostate cancer (PCa) has contributed to the reduction in mortality observed for this disease in the United States over the past several years (1). However, results from two large randomized trials in Europe and the US provide strong evidence that PSA-based screening for PCa is associated with a high risk of overdiagnosis (2,3). In the European trial, PSA screening was associated with decreased PCa related mortality but at a great cost: ~1,410 men needed to be screened, and 48 additional PCa cases would need to be treated to prevent one death from PCa (2). Although interpretation of these findings is still a subject of discussion, the current inability to accurately distinguish risk for life-threatening, aggressive PCa from the overwhelming majority of indolent cases contributes to the dilemma.

Recent breakthroughs in genome-wide association studies (GWAS) have led to the discovery of more than two dozen reported single nucleotide polymorphisms (SNPs) that are associated with PCa risk by comparing men with and without PCa using case-control study designs (6-25). Unfortunately, none of these PCa risk associated SNPs consistently distinguishes risk for more or less aggressive cancer (26-28), nor are they associated with prostate cancer-specific mortality (29). As a result, there has been much debate regarding the clinical utility of these SNPs as a risk stratification tool (30,31). Clearly, an alternative approach is needed to identify genetic markers that distinguish those men who are at risk for developing more aggressive PCa.

The present invention overcomes previous shortcomings in the art by identifying significant statistical associations between genetic markers and prostate cancer. Thus, the present invention provides methods and compositions for identifying a subject at increased risk of developing aggressive prostate cancer by detecting the genetic markers of this invention in the subject.

SUMMARY OF THE INVENTION

The present invention provides a method of identifying a human subject as having an increased risk of developing aggressive prostate cancer, comprising detecting in a nucleic acid sample from the subject a T allele at single nucleotide polymorphism rs4054823 in chromosome region 17p12, wherein the detection of said allele identifies the subject as having an increased risk of developing aggressive prostate cancer.

Also provided herein is a method of identifying a human subject as having an increased risk of developing aggressive prostate cancer, comprising detecting in a nucleic acid sample from the subject an allele that is in linkage disequilibrium with the T allele at single nucleotide polymorphism rs4054823 in chromosome region 17p12, wherein the detection of said allele identifies the subject as having an increased risk of developing aggressive prostate cancer.

Furthermore, the present invention provides a kit containing oligonucleotides and other reagents for detecting an allele or combination of alleles of this invention.

Additionally provide herein is a computer-assisted method of identifying a proposed treatment for aggressive prostate cancer as an effective and/or appropriate treatment for a subject carrying a genetic marker correlated with aggressive prostate cancer, comprising the steps of: (a) storing a database of biological data for a plurality of subjects, the biological data that is being stored including for each of said plurality of subjects: (i) a treatment type, (ii) at least one genetic marker associated with aggressive prostate cancer, and (iii) at least one disease progression measure for prostate cancer from which treatment efficacy can be determined; and then (b) querying the database to determine the dependence on said genetic marker of the effectiveness of a treatment type in treating prostate cancer, thereby identifying a proposed treatment as an effective and/or appropriate treatment for a subject carrying a genetic marker correlated with prostate cancer.

DETAILED DESCRIPTION OF THE INVENTION

Figure 1:
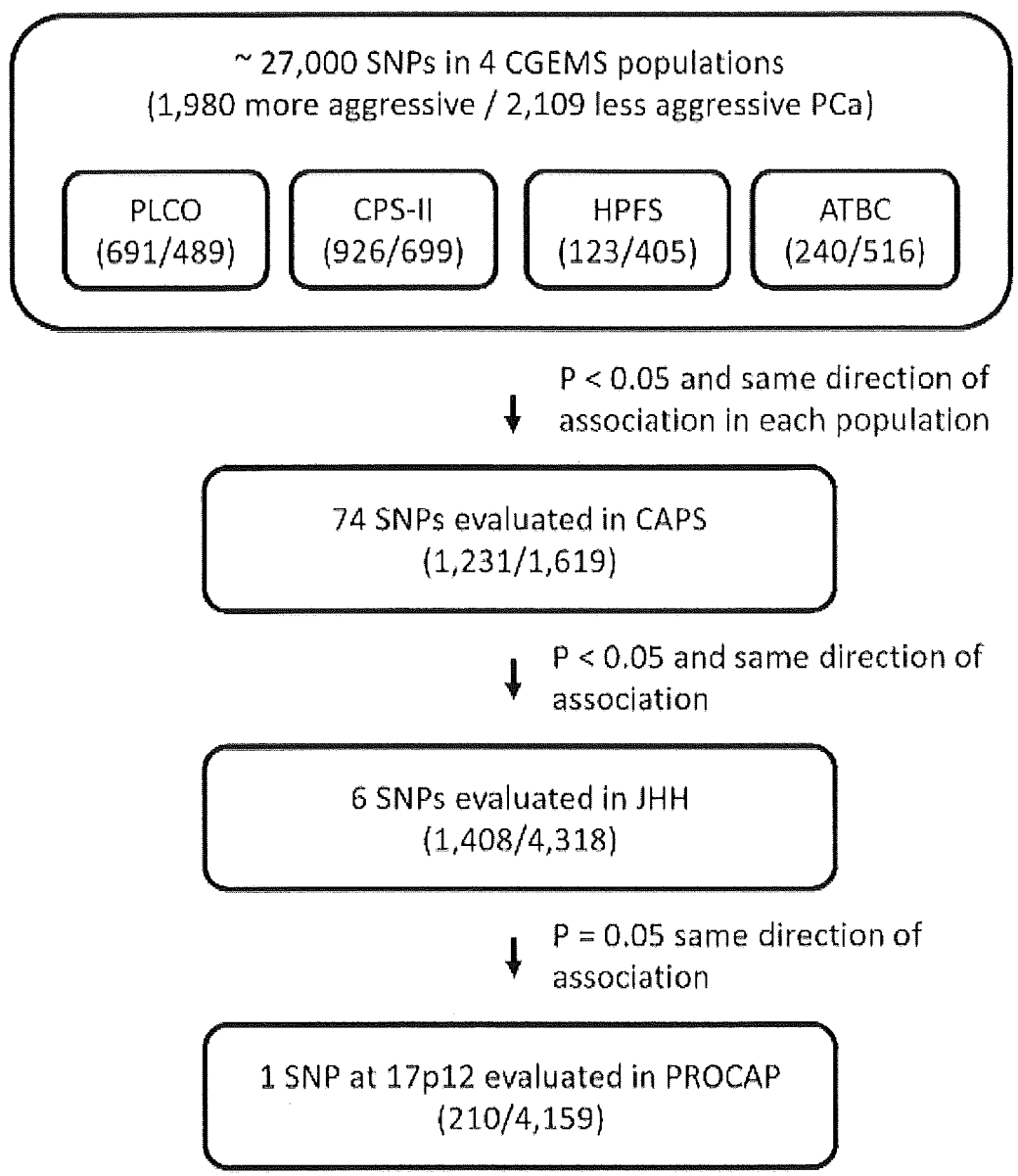
FIG. 1. Flow chart of the study design. Numbers of subjects with more or less aggressive prostate cancer in each study population are indicated in parentheses.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery of particular alleles of single nucleotide polymorphisms (SNPs) that are statistically associated with an increased risk of developing aggressive prostate cancer. There are numerous benefits of carrying out the methods of this invention to identify a subject having an increased risk of developing aggressive prostate cancer, including but not limited to, identifying subjects who are good candidates for prophylactic and/or therapeutic treatment, and screening for cancer at an earlier time or more frequently than might otherwise be indicated, to increase the chances of early detection of an aggressive prostate cancer.

Thus, in one aspect, the present invention provides a method of identifying a subject (e.g., a human subject) as having an increased risk of developing aggressive prostate cancer, comprising detecting in a nucleic acid sample from the subject a T allele at single nucleotide polymorphism rs4054823 in chromosome region 17p12, wherein the detection of said alleles identifies the subject as having an increased risk of developing aggressive prostate cancer.

The present invention further provides a method of identifying a subject as having an increased risk of developing aggressive prostate cancer, comprising detecting in a nucleic acid sample from the subject an allele in linkage disequilibrium (LD) with the T allele at single nucleotide polymorphism rs4054823 in chromosome region 17p12. Alleles in LD with the T allele at single nucleotide polymorphism rs4054823 in chromosome region 17p12 are provided herein in Table 1. Such alleles can be detected individually (e.g., detection of a risk allele at a single SNP location) as well as in any combination (e.g., detection of a risk allele at more than one (e.g., 2, 3, 4, 5, 6, 7, 8, 9, 10, etc.) SNP location). In some embodiments, when analyzed in combination, the combination can comprise detection of the T allele at rs4054823 in addition to detection of one or more of the alleles of Table 1. In some embodiments, the combination can be a (e.g., any) combination of the alleles of Table 1 without the T allele of rs4054823.

In some embodiments of this invention, the subject can be homozygous for the T allele at single nucleotide polymorphism rs4054823 in chromosome region 17p12. In other embodiments, the subject can be heterozygous for the T allele at single nucleotide polymorphism rs4054823 in chromosome region 17p12. The presence of the T allele, either homozygously or heterozygously, at single nucleotide polymorphism rs4054823 in chromosome region 17p12 identifies the subject as having an increased risk of developing aggressive prostate cancer. In the methods provided herein wherein a combination of alleles is analyzed, the subject can be heterozygous or homozygous for any given allele in any combination relative to the other alleles in the combination.

In certain embodiments of this invention, the methods described herein can be employed to identify 1) a subject at increased or decreased risk of a more aggressive form of prostate cancer (e.g., having a Gleason score of 7 (4+3) to 10), 2) a subject at increased or decreased risk of a poor prognosis (e.g., increased likelihood the cancer will metastasize, will be poorly responsive to treatment and/or will lead to death) once cancer has been diagnosed in the subject; and/or 3) a subject at increased or decreased risk of an early age of onset of prostate cancer (e.g., aggressive prostate cancer), by identifying in the subject the alleles of this invention.

It is further contemplated that the methods of this invention can be carried out to diagnose aggressive prostate cancer in a subject, by detecting the T allele of SNP rs4054823 and/or detecting any combination of the alleles of this invention in nucleic acid from the subject.

In further aspects, the present invention provides a kit for carrying out the methods of this invention, wherein the kit can comprise oligonucleotides (e.g., primers, probes, primer/probe sets, etc.), reagents, buffers, etc., as would be known in the art, for the detection of the alleles of this invention in a nucleic acid sample. For example, a primer or probe can comprise a contiguous nucleotide sequence that is complementary (e.g., fully (100%) complementary or partially (50%, 60%, 70%, 80%, 90%, 95%, etc.) complementary) to a region comprising an allele of this invention. In particular embodiments, a kit of this invention will comprise primers and probes that allow for the specific detection of the alleles of this invention. Such a kit can further comprise blocking probes, labeling reagents, blocking agents, restriction enzymes, antibodies, sampling devices, positive and negative controls, etc., as would be well known to those of ordinary skill in the art. Thus, in some embodiments, the present invention provides a kit comprising oligonucleotides to detect the T allele of single nucleotide polymorphism rs4054823 in chromosome region 17p12 in a nucleic acid sample. In further embodiments, the present invention provides a kit comprising oligonucleotides to detect an allele or combination of alleles in linkage disequilibrium with the T allele of single nucleotide polymorphism rs4054823 in chromosome region 17p12 in a nucleic acid sample, such as the alleles set forth in Table 1 herein. Such oligonucleotides can be identified and prepared and employed in methods according to the teachings and protocols described herein and as are well known in the art.

Definitions

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

As used herein, the term "prostate cancer" or "PCa" describes an uncontrolled (malignant) growth of cells in the prostate gland, which is located at the base of the urinary bladder and is responsible for helping control urination as well as forming part of the semen. Symptoms of prostate cancer can include, but are not limited to, urinary problems (e.g., not being able to urinate; having a hard time starting or stopping the urine flow; needing to urinate often, especially at night; weak flow of urine; urine flow that starts and stops; pain or burning during urination), difficulty having an erection, blood in the urine and/or semen, and/or frequent pain in the lower back, hips, and/or upper thighs.

As used herein, the term "aggressive prostate cancer" means prostate cancer that is poorly differentiated, having a Gleason grade of 7 or above. An "indolent prostate cancer" means prostate cancer having a Gleason grade below 7 (e.g., 6 or less). The Gleason grading system is the most commonly used method for grading PCa and is well known in the art.

All the SNP positions described herein are based on Build 36.

The term "chromosome region" as used herein refers to a part of a chromosome defined either by anatomical details, especially by banding, or by its linkage groups. The particular chromosome region of this invention is 17p12.

Also as used herein, "linked" describes a region of a chromosome that is shared more frequently in family members or members of a population manifesting a particular phenotype and/or affected by a particular disease or disorder, than would be expected or observed by chance, thereby indicating that the gene or genes or other identified marker(s) within the linked chromosome region contain or are associated with an allele that is correlated with the phenotype and/or presence of a disease or disorder (e.g., aggressive PCa), or with an increased or decreased likelihood of the phenotype and/or of the disease or disorder. Once linkage is established, association studies (linkage disequilibrium) can be used to narrow the region of interest or to identify the marker (e.g., allele or haplotype) correlated with the phenotype and/or disease or disorder.

Furthermore, as used herein, the term "linkage disequilibrium" or "LD" refers to the occurrence in a population of two or more (e.g., 2, 3, 4, 5, 6, 7, 8, 9, 10, etc.) linked alleles at a frequency higher or lower than expected on the basis of the gene frequencies of the individual genes. Thus, linkage disequilibrium describes a situation where alleles occur together more often than can be accounted for by chance, which indicates that the two or more alleles are physically close on a DNA strand.

The term "genetic marker" or "polymorphism" as used herein refers to a characteristic of a nucleotide sequence (e.g., in a chromosome) that is identifiable due to its variability among different subjects (i.e., the genetic marker or polymorphism can be a single nucleotide polymorphism an allele of a single nucleotide polymorphism, a restriction fragment length polymorphism, a microsatellite, a deletion of nucleotides, an addition of nucleotides, a substitution of nucleotides, a repeat or duplication of nucleotides, a translocation of nucleotides, and/or an aberrant or alternate splice site resulting in production of a truncated or extended form of a protein, etc., as would be well known to one of ordinary skill in the art).

A "single nucleotide polymorphism" (SNP) in a nucleotide sequence is a genetic marker that is polymorphic for two (or in some case three or four) alleles. SNPs can be present within a coding sequence of a gene, within noncoding regions of a gene and/or in an intergenic (e.g., intron) region of a gene. A SNP in a coding region in which both forms lead to the same polypeptide sequence is termed synonymous (i.e., a silent mutation) and if a different polypeptide sequence is produced, the alleles of that SNP are non-synonymous. SNPs that are not in protein coding regions can still have effects on gene splicing, transcription factor binding and/or the sequence of non-coding RNA.

The SNP nomenclature provided herein refers to the official Reference SNP (rs) identification number as assigned to each unique SNP by the National Center for Biotechnological Information (NCBI), which is available in the GenBank® database.

In some embodiments, the term genetic marker is also intended to describe a phenotypic effect of an allele or haplotype, including for example, an increased or decreased amount of a messenger RNA, an increased or decreased amount of protein, an increase or decrease in the copy number of a gene, production of a defective protein, tissue or organ, etc., as would be well known to one of ordinary skill in the art.

An "allele" as used herein refers to one of two or more alternative forms of a nucleotide sequence at a given position (locus) on a chromosome (e.g., at a single nucleotide polymorphism). An allele can be a nucleotide present in a nucleotide sequence that makes up the coding sequence of a gene and/or an allele can be a nucleotide in a non-coding region of a gene (e.g., in a genomic sequence). A subject's genotype for a given gene is the set of alleles the subject happens to possess. As noted herein, an individual can be heterozygous or homozygous for any allele of this invention.

Also as used herein, a "haplotype" is a set of alleles on a single chromatid that are statistically associated. It is thought that these associations, and the identification of a few alleles of a haplotype block, can unambiguously identify all other alleles in its region. The term "haplotype" is also commonly used to describe the genetic constitution of individuals with respect to one member of a pair of allelic genes; sets of single alleles or closely linked genes that tend to be inherited together.

The terms "increased risk" and "decreased risk" as used herein define the level of risk that a subject has of developing aggressive prostate cancer, as compared to a control subject that does not have the alleles of this invention in the control subject's nucleic acid.

A sample of this invention can be any sample containing nucleic acid from a subject, as would be well known to one of ordinary skill in the art. Nonlimiting examples of a sample of this invention include a cell, a body fluid, a tissue, biopsy material, a washing, a swabbing, etc., as would be well known in the art.

A subject of this invention is any animal that is susceptible to prostate cancer as defined herein and can include, for example, humans, as well as animal models of prostate cancer (e.g., rats, mice, dogs, nonhuman primates, etc.). In some aspects of this invention, the subject can be Caucasian (e.g., white; European-American; Hispanic), as well as of black African ancestry (e.g., black; African, Sub-Saharan African, African American; African-European; African-Caribbean, etc.) or Asian. In further aspects of this invention, the subject can have a family history of prostate cancer or aggressive prostate cancer (e.g., having at least one first degree relative having or diagnosed with prostate cancer or aggressive prostate cancer) and in some embodiments, the subject does not have a family history of prostate cancer or aggressive prostate cancer. Additionally a subject of this invention can have a diagnosis of prostate, cancer or aggressive prostate cancer in certain embodiments and in other embodiments, a subject of this invention does not have a diagnosis of prostate cancer or aggressive prostate cancer. In yet further embodiments, the subject of this invention can have an elevated prostate-specific antigen (PSA) level and in other embodiments, the subject of this invention can have a normal or non-elevated PSA level. In some embodiments, the PSA level of the subject may not be known and/or has not been measured.

As used herein, "nucleic acid" encompasses both RNA and DNA, including cDNA, genomic DNA, mRNA, synthetic (e.g., chemically synthesized) DNA and chimeras, fusions and/or hybrids of RNA and DNA. The nucleic acid can be double-stranded or single-stranded. Where single-stranded, the nucleic acid can be a sense strand or an antisense strand. In some embodiments, the nucleic acid can be synthesized using oligonucleotide analogs or derivatives (e.g., inosine or phosphorothioate nucleotides, etc.). Such oligonucleotides can be used, for example, to prepare nucleic acids that have altered base-pairing abilities or increased resistance to nucleases.

An "isolated nucleic acid" is a nucleotide sequence that is not immediately contiguous with nucleotide sequences with which it is immediately contiguous (one on the 5' end and one on the 3' end) in the naturally occurring genome of the organism from which it is derived or in which it is detected or identified. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid or polypeptide that is substantially free of cellular material, viral material, and/or culture medium (e.g., when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., as are well known in the art.

The present invention further provides fragments of the nucleic acids of this invention, which can be used, for example, as oligonucleotides, primers and/or probes. Such fragments or oligonucleotides can be detectably labeled or modified, for example, to include and/or incorporate a restriction enzyme cleavage site when employed as a primer in an amplification (e.g., PCR) assay.

The detection of a polymorphism, genetic marker or allele of this invention can be carried out according to various protocols standard in the art and as described herein for analyzing nucleic acid samples and nucleotide sequences, as well as identifying specific nucleotides in a nucleotide sequence.

For example, nucleic acid can be obtained from any suitable sample from the subject that will contain nucleic acid and the nucleic acid can then be prepared and analyzed according to well-established protocols for the presence of genetic markers according to the methods of this invention. In some embodiments, analysis of the nucleic acid can be carried by amplification of the region of interest according to amplification protocols well known in the art (e.g., polymerase chain reaction, ligase chain reaction, strand displacement amplification, transcription-based amplification, self-sustained sequence replication (3SR), Qβ replicase protocols, nucleic acid sequence-based amplification (NASBA), repair chain reaction (RCR) and boomerang DNA amplification (BDA), etc.). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

In some embodiments of this invention, detection of an allele or combination of alleles of this invention can be carried out by an amplification reaction and single base extension. In particular embodiments, the product of the amplification reaction and single base extension is spotted on a silicone chip.

In yet additional embodiments, detection of an allele or combination of alleles of this invention can be carried out by matrix-assisted laser desorption/ionization-time of flight mass spectrometry (MALDI-TOF-MS).

It is further contemplated that the detection of an allele or combination of alleles of this invention can be carried out by various methods that are well known in the art, including, but not limited to nucleic acid sequencing, hybridization assay, restriction endonuclease digestion analysis, electrophoresis, and any combination thereof.

The genetic markers (e.g., alleles) of this invention are correlated with (i.e., identified to be statistically associated with) aggressive prostate cancer as described herein according to methods well known in the art and as disclosed in the Examples provided herein for statistically correlating genetic markers with various phenotypic traits, including disease states and pathological conditions as well as determining levels of risk associated with developing a particular phenotype, such as a disease or pathological condition. In general, identifying such correlation involves conducting analyses that establish a statistically significant association and/or a statistically significant correlation between the presence of a genetic marker or a combination of markers and the phenotypic trait in a population of subjects and controls (e.g., a population of subjects in whom the phenotype is not present or has not been detected). The correlation can involve one or more than one genetic marker of this invention (e.g., two, three, four, five, or more) in any combination. An analysis that identifies a statistical association (e.g., a significant association) between the marker or combination of markers and the phenotype establishes a correlation between the presence of the marker or combination of markers in a population of subjects and the particular phenotype being analyzed. A level of risk (e.g., increased or decreased) can then be determined for an individual on the basis of such population-based analyses.

Thus, in certain embodiments, the present invention provides a method of screening a subject for a genetic marker (e.g., an allele at a SNP site) that is associated with aggressive prostate cancer, comprising: a) performing a population based study to detect polymorphisms (e.g., alleles) in a group of subjects with aggressive prostate cancer and a group of control subjects; b) identifying polymorphisms in the aggressive prostate cancer group of subjects that are statistically associated with the presence of aggressive prostate cancer; and c) screening a subject for the presence of the polymorphisms identified in step (b).

The present invention further provides a method of identifying an effective and/or appropriate (i.e., for a given subject's particular condition or status) treatment regimen for a subject with aggressive prostate cancer, comprising detecting one or more of the polymorphisms and genetic markers associated with aggressive prostate cancer of this invention in the subject, wherein the one or more polymorphisms and genetic markers are further statistically correlated with an effective and/or appropriate treatment regimen for aggressive prostate cancer according to protocols as described herein and as are well known in the art.

Also provided is a method of identifying an effective and/or appropriate treatment regimen for a subject with aggressive prostate cancer, comprising: a) correlating the presence of one or more genetic markers of this invention in a test subject or population of test subjects with aggressive prostate cancer for whom an effective and/or appropriate treatment regimen has been identified; and b) detecting the one or more markers of step (a) in the subject, thereby identifying an effective and/or appropriate treatment regimen for the subject.

Further provided is a method of correlating a polymorphism or genetic marker of this invention with an effective and/or appropriate treatment regimen for aggressive prostate cancer, comprising: a) detecting in a subject or a population of subjects with aggressive prostate cancer and for whom an effective and/or appropriate treatment regimen has been identified, the presence of one or more genetic markers or polymorphisms of this invention; and b) correlating the presence of the one or more genetic markers of step (a) with an effective treatment regimen for aggressive prostate cancer.

Examples of treatment regimens for prostate cancer are well known in the art. Subjects who respond well to particular treatment protocols can be analyzed for specific genetic markers and a correlation can be established according to the methods provided herein. Alternatively, subjects who respond poorly to a particular treatment regimen can also be analyzed for particular genetic markers correlated with the poor response. Then, a subject who is a candidate for treatment for aggressive prostate cancer can be assessed for the presence of the appropriate genetic markers and the most effective and/or appropriate treatment regimen can be provided as early as possible.

In some embodiments, the methods of correlating genetic markers with treatment regimens of this invention can be carried out using a computer database. Thus the present invention provides a computer-assisted method of identifying a proposed treatment for aggressive prostate cancer and/or appropriate treatment for a subject carrying a genetic marker correlated with aggressive prostate cancer. The method involves the steps of (a) storing a database of biological data for a plurality of subjects, the biological data that is being stored including for each of said plurality of subjects, for example, (i) a treatment type, (ii) at least one genetic marker associated with aggressive prostate cancer and (iii) at least one disease progression measure for aggressive prostate cancer from which treatment efficacy can be determined; and then (b) querying the database to determine the correlation between the presence of said genetic marker and the effectiveness of a treatment type in treating aggressive prostate cancer, to thereby identify a proposed treatment as an effective for aggressive prostate cancer and/or an appropriate treatment for a subject carrying a genetic marker correlated with aggressive prostate cancer. In such methods, the genetic marker associated with aggressive prostate cancer can be a T allele in single nucleotide polymorphism rs4054823 in chromosome region 17p12.

In some embodiments, treatment information for a subject is entered into the database (through any suitable means such as a window or text interface), genetic marker information for that subject is entered into the database, and disease progression information is entered into the database. These steps are then repeated until the desired number of subjects has been entered into the database. The database can then be queried to determine whether a particular treatment is effective for subjects carrying a particular marker or combination of markers, not effective for subjects carrying a particular marker or combination of markers, etc. Such querying can be carried out prospectively or retrospectively on the database by any suitable means, but is generally done by statistical analysis in accordance with known techniques, as described herein.

The following examples are not intended to limit the scope of the claims to the invention, but are rather intended to be exemplary of certain embodiments. Any variations in the exemplified methods that occur to the skilled artisan are intended to fall within the scope of the present invention. As will be understood by one skilled in the art, there are several embodiments and elements for each aspect of the claimed invention, and all combinations of different elements are hereby anticipated, so the specific combinations exemplified herein are not to be construed as limitations in the scope of the invention as claimed. If specific elements are removed or added to the group of elements available in a combination, then the group of elements is to be construed as having incorporated such a change.

EXAMPLES

Abstract.

Autopsy studies suggest that most aging men will develop lesions that, if detected clinically, would be diagnosed as prostate cancer (PCa). Most of these cancers are indolent and remain localized; however, a subset of PCa is aggressive and accounts for more than 27,000 deaths in the United States annually. Identification of factors specifically associated with risk for more aggressive PCa is urgently needed to reduce overdiagnosis and overtreatment of this common disease. To search for such factors, the frequencies of SNPs were compared among PCa patients who were defined as having either more aggressive or less aggressive disease in four populations examined in the Genetic Markers of Susceptibility (CGEMS) study performed by the National Cancer Institute. SNPs showing possible associations with disease severity were further evaluated in an additional three independent study populations from the United States and Sweden. In total, 4,829 and 12,205 patients with more and less aggressive disease, respectively, were studied. It was found that the frequency of the TT genotype of SNP rs4054823 at 17p12 was consistently higher among patients with more aggressive compared with less aggressive disease in each of the seven populations studied, with an overall P value of $2.1 \times 10^{-8}$ under a recessive model, exceeding the conservative genome-wide significance level. The difference in frequency was largest between patients with high-grade, non-organ-confined disease compared with those with low-grade, organ-confined disease. This study demonstrates that inherited variants predisposing to aggressive but not indolent PCa exist in the genome and demonstrates the clinical potential of such variants as potential early markers for risk of aggressive PCa.

Study Subjects.

Seven independent populations were included in this study (Table 2). The first four populations were from the publicly available CGEMS study, and include the Prostate, Lung, Colon and Ovarian (PLCO) Cancer Screening Trial, the American Cancer Society Cancer Prevention Study II (CPS-II), the Health Professionals Follow-up Study (HPFS), and the Alpha-Tocopherol, Beta-Carotene Cancer Prevention Study (ATBC) (9, 11). PCa aggressiveness was defined by the CGEMS study as follows: patients with clinical stage T3/T4 or Gleason score of 7 or higher (stage and grade designations as described herein) based on biopsy specimens were classified as having more aggressive disease, whereas the remaining patients were classified as having less aggressive disease.

The other three populations were from our collaborative research group, including a hospital-based case series from the Johns Hopkins Hospital (JHH), and two population-based studies based on the National Prostate Cancer Register of Sweden; a case-control study; CAncer Prostate in Sweden (CAPS) (41, 26), and a case series of PCa patients treated for localized PCa (PROCAP) (42, 43).

PCa patients from the CAPS study were identified and recruited from four regional cancer registries in Sweden, diagnosed between July 2001 and October 2003. Patients were classified as having more aggressive disease if their cancers met any of the following criteria: advanced stage as evidenced by disease spread outside of the prostate; presence of cancer in the lymph nodes or other metastatic sites (clinical stage T3/T4, N+, M+, respectively); presence of poorly differentiated cancer at biopsy as indicated by a high Gleason score (i.e., 4+4=8 or higher; Gleason scores are the sum of the two most prevalent histologic patterns, rated on a scale of 1-5, with 5 being the most poorly differentiated); or a serum PSA level associated with a high likelihood of extensive disease (>50 ng/mL (n=1,231). Otherwise, the patients were classified as having less aggressive disease (n=1,619) (Table 4).

The PCa patients from the JHH study were men who underwent radical prostatectomy for treatment of PCa at JHH from Jan. 1, 1999, through Dec. 31, 2008. Because of the non-JHH populations analyzed in this study including only individuals of European descent, the JHH population was similarly confined. Tumors were graded and staged after resection; those with Gleason scores of 7, with the most prevalent pattern being 4, or higher, or stage T3b or higher, or N+ or M+ were defined as more aggressive disease (n=1,408). Tumors with Gleason score of 7 with most prevalent pattern 3, or lower and no evidence of disease dissemination (pathologic stage T2/N0/M0) were defined as having less aggressive disease (n=4,318) (Table 5).

The PROCAP study was a cohort of PCa patients diagnosed predominantly with clinically localized disease between 1997 and 2002 and recruited from the National Prostate Cancer Register of Sweden. Among 4,356 patients, 210 were classified as having more aggressive disease (clinical stage T3/T4, N+, M+, Gleason Score≥8, or pretreatment serum PSA≥50 ng/mL). The remaining 4,159 patients were classified as having less aggressive disease.

SNPs and Genotyping Methods.

The genotyping data for ~27,000 SNPs in four CGEMS study populations (PLCO, CPS-II, HPFS, and ATBC) were publically available. These SNPs were genotyped because they were significantly associated with PCa risk in the first-stage GWAS of the CGEMS study (PLCO) using a case-control analysis (11). Individual genotype data from PLCO were obtained through an approved data request application. Summary genotype information from CPS-II, HPFS, and ATBC were downloaded from a publicly accessible CGEMS website (cgems.cancer.gov/data/).

SNP genotyping in the CAPS, JHH, and PROCAP subjects was performed using the MassARRAY iPLEX genotyping system (Sequenom) at Wake Forest University. Duplicate test samples and two water samples (PCR negative controls) that were blinded to the technician were included in each 96-well plate. The rate of concordant results between 100 duplicate samples was >99%.

Statistical Analysis.

Allele frequency differences between two groups of patients were tested for each SNP using a $\chi^2$ test with 1 degree of freedom within each population. The allelic odds ratio (OR) and 95% confidence interval (95% CI) were estimated based on a multiplicative model. Genotype frequency differences between two groups of patients were also tested using both a dominant and a recessive model for SNPs that were confirmed in an allele test from multiple populations. Results from multiple populations were combined using a Mantel-Haenszel model in which the populations were allowed to have different allele frequencies but were assumed to have a common OR. The homogeneity of ORs among different study populations was tested using Breslow-Day $\chi^2$ test.

For SNPs that were confirmed to be significantly associated with aggressiveness of PCa, a $\chi^2$ test using a 2×K table was performed for Gleason scores and T-stage, in which K is the number of possible categories within each variable. All reported P values were based on a two-sided test.

To identify inherited genetic markers that are associated with aggressiveness of PCa, publicly available genotype data were analyzed for ~27,000 SNPs across the genome among 1,980 patients with more aggressive disease and 2,109 patients with less aggressive disease from four CGEMS study populations (PLCO, CPS-II, HPFS, and ATBC) using a case-case analysis (FIG. 1, Table 2). Based on the results of a combined allelic test, a subset of SNPs (n=74) was selected for further evaluation, where P<0.05 for the difference between more and less aggressive disease, and the direction of association was consistent among the four studies. These SNPs were subsequently evaluated in an independent cohort of 1,231 patients with more aggressive disease and 1,619 patients with less aggressive disease from the CAPS study (Table 4). Six of these 74 SNPs were confirmed; P<0.05 for the allelic test, with the same direction of association (Table 7). These six SNPs were then evaluated in 1,408 patients with more aggressive disease and 4,318 patients with less aggressive disease from the Johns Hopkins Hospital (JHH) study population (Table 5). One SNP (rs4054823 at 17p12) had a marginally different allele frequency between the two types of PCa patients (P=0.051), with the same direction of association as in the previous studies (Table 8). This SNP was further evaluated in an additional independent Swedish PCa patient population (PROCAP), comprising 210 patients with more aggressive disease and 4,159 patients with less aggressive disease. The allelic test confirmed the association (P=0.01).

As summarized in Table 3, the frequency of allele T of SNP rs4054823 was consistently higher in patients with more aggressive disease compared with patients with less aggressive disease in each of the four CGEMS populations, and was significant in the combined allelic test (P=9.8× $10^{-4}$). The T allele of rs4054823 was also more frequent in patients with more aggressive disease in each of the three independent populations in the confirmation stage, with a value of P=5.0×$10^{-4}$ from a combined allelic test. Combining the data from all seven populations, the allelic test of the SNP and aggressiveness of PCa was highly significant ($P=2.1\times10^{-6}$). When genotype frequencies of this SNP between the two types of PCa were tested using dominant and recessive models, the recessive model (allele T) was most significant ($P=2.1\times10^{-8}$). This P value exceeded a study-wide significance level at a 5% false positive rate using a conservative Bonferroni correction (27,000 SNPs and three genetic models). The TT genotype was found in 32% of 4829 cases with aggressive disease and 28% of 12,205 cases with less aggressive disease. Compared with PCa patients who had CC or CT genotypes, patients who had the TT genotype of this SNP had an odds ratio (OR) of 1.26 (95% confidence interval [CI], 1.16-1.36) for aggressive PCa. No heterogeneity was observed in the OR estimates among different populations (P=0.56, Breslow-Day test).

Figure 2:
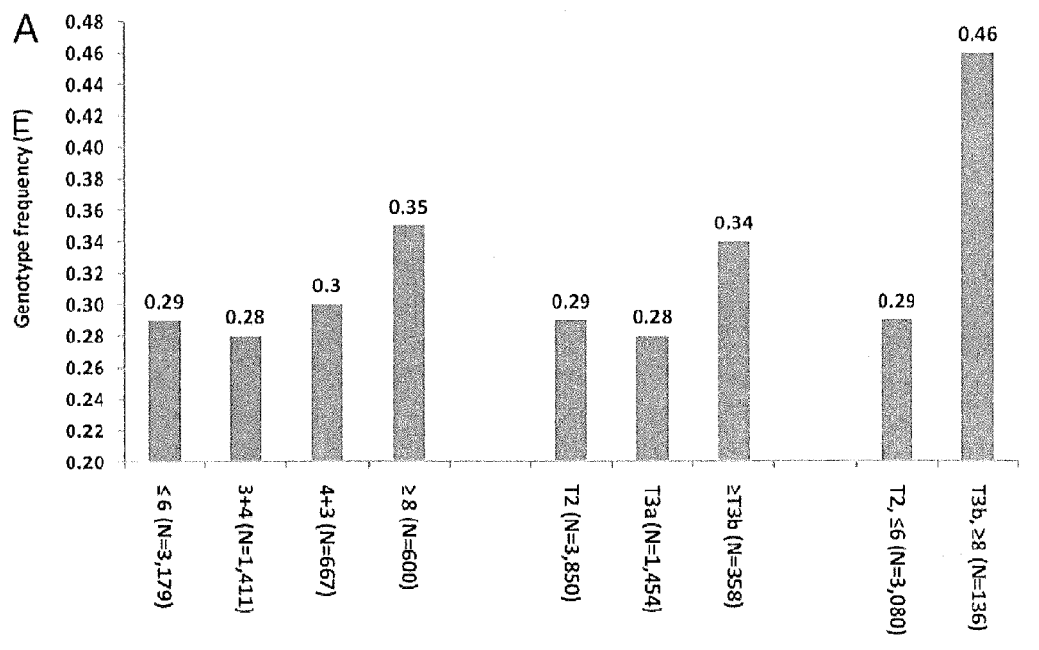
FIG. 2. Frequency of TT genotype of rs4054823 at 17p12 among PCa patients from the (A) JHH population and (B) CAPS population of Sweden.
Figure 2:
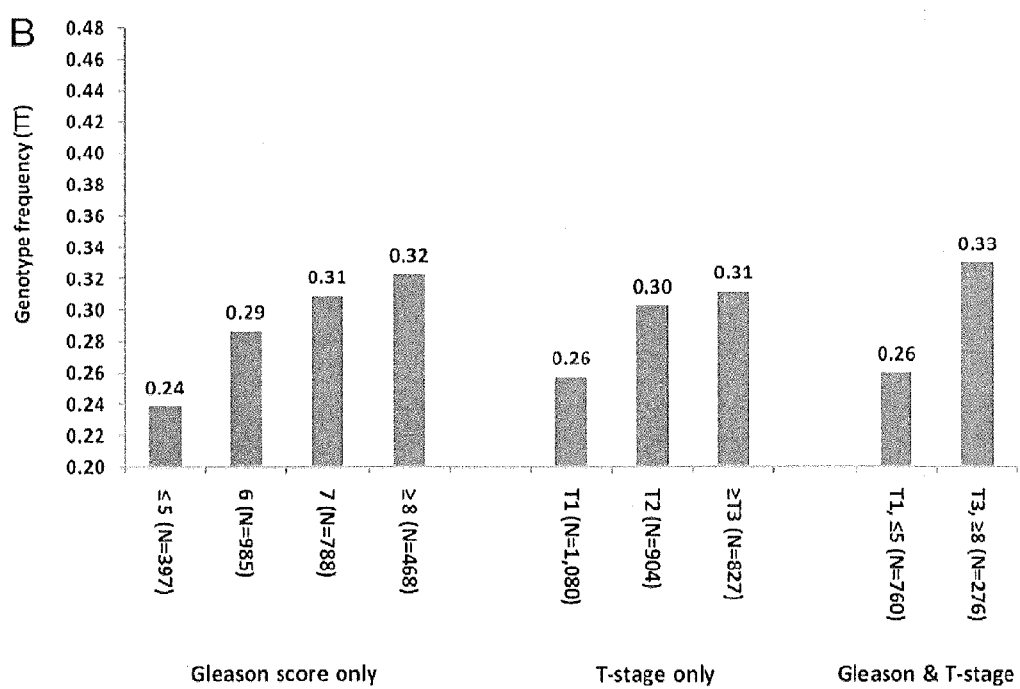

To overcome potential limitations arising from the heterogeneous definitions of aggressive PCa used among these seven study populations, and to more fully characterize the association, an in-depth analysis was performed of the correlation of SNP rs4054823 with specific clinicopathologic variables of PCa including tumor grade as assessed by Gleason score and TNM stage in populations for which this information was available. This analysis was first performed in patients from JHH for the following reasons: (i) a large number of patients (n=5,955) recruited from the same hospital were available; (ii) all patients were treated with radical prostatectomy and thus, unlike patients receiving either no or nonsurgical treatment, their tumors were available for extensive pathologic evaluation; and (iii) tumors were uniformly graded and staged by pathologists at JHH using the same protocol (32, 33). In this analysis, it was found that the frequency of the TT genotype was lower in patients with well-to moderately differentiated cancers (29%, 28%, and 30% in cancers with Gleason scores≤6, 3+4, and 4+3, respectively) and increased only in patients with more poorly differentiated tumors, i.e., Gleason scores≥8 (35%), P=0.002 from a $\chi^2$ test comparing patients with Gleason score≥8 and <8 (FIG. 2A). Similarly, it was found that the frequency of the TT genotype was lower in patients with low disease stage (pT2, 29% and pT3a, 28%) and was increased in patients with higher disease stage (≥pT3b, 34%; P=0.03, from a $\chi^2$ test comparing patients with stage≥pT3b and <pT3b). The difference in TT genotype frequency was largest between the most extreme groups with regard to likelihood of disease progression and lethality: 29% of patients with the least aggressive disease (Gleason score≤6 and organ-confined stage, pT2, n=3,080), compared with 46% of patients with the most aggressive PCa (Gleason score≥8 and non-organ-confined stage, ≥pT3b, n=136; OR=2.11; 95% CI: 1.507-2.99), $P=1.6\times10^{-5}$.

The association of this SNP with clinicopathologic variables was also examined in the Swedish CAPS population, although this population differed from the JHH population in that the treatments included multiple modalities (none, radiation, surgery, and hormonal), resulting in less uniform tumor staging and grading. In this population, the TT genotype frequency also increased with increasing Gleason score and stage; the largest difference was between the most and least aggressive PCa patients (FIG. 2B). The pattern of association, however, differed from that of JHH: a threshold increase of TT genotype frequency in patients with Gleason score≥8 or stage≥pT3b was observed in the JHH patients, whereas a gradual increase of TT genotype frequency was observed with increasing Gleason score or stage in CAPS patients. This difference may be due to the pathologic evaluation of prostatectomy specimens in the JHH study versus the clinical grading of biopsy specimens and clinical staging of the majority of cases in the CAPS study. Typically, a ~20-30% discrepancy in grading and staging is observed between clinical and pathologic evaluations of the same patient (34).

This study reflects an important shift in genetic association studies of PCa. Most studies to date have searched for inherited genetic variants that predispose men to overall PCa risk, by comparing men with and without PCa using a case-control design. In contrast, this study was strategically designed to identify inherited genetic markers that distinguish between risk for aggressive versus indolent PCa, by comparing SNPs among PCa patients with these two disease phenotypes using a case-case design. The need for this change in approach is supported by several trends, including a concern over increased rates of diagnosis and treatment of indolent disease and the lack of consistently validated markers of aggressive disease identified using currently used case-control study designs (26).

In this study, a SNP has been identified with a genotype frequency that is consistently different between patients with more or less aggressive PCa in each of the seven independent populations studied. The difference between the two types of PCa was statistically significant ($P=2.1\times10^{-8}$), exceeding a conservative study-wide and even genome-wide significance level. More importantly, the difference in frequency was largest between patients with high-grade, non-organ-confined disease and thus at high risk for adverse outcomes compared with patients with low-risk, low-grade, organ-confined disease.

It is of interest to note that the frequency of the TT genotype of SNP rs4054823 in unaffected controls is similar to that observed in less aggressive cases (Table 6), and is significantly higher only among more aggressive cases. This observation implicates such SNPs as not only being informative of risk for aggressive PCa at the time of diagnosis, but also before diagnosis, to possibly target men for more effective PSA screening based on their risk for clinically important PCa.

Based on this study, it is envisioned that a panel of SNPs with characteristics similar to the one described here could be an important part of a genetic-based, targeted PSA screening strategy that is effective in reducing the number of men requiring disease screening, thereby reducing overdiagnosis while also decreasing mortality by facilitating identification of those men at risk for aggressive PCa at a stage when the disease is potentially curable.

All publications and patent applications, nucleotide sequences and/or amino acid sequences identified by GenBank® Database Accession numbers are herein incorporated by reference to the same extent as if each individual publication or patent application or sequences was specifically and individually indicated to be incorporated by reference.

Although the foregoing invention has been described in some detail by way of illustration and example for purposes of clarity of understanding, it will be apparent that certain changes and modifications may be practiced within the scope of the list of the foregoing embodiments and the appended claims.

REFERENCES

1. Jemal et al. (2009) Cancer statistics. 2009. *CA Cancer J Clin* 59:225-249.
2. Schröder et al. ERSPC Investigators (2009) Screening and prostate-cancer mortality in a randomized European study. *N Engl J Med* 360:1320-1328.

3. Andriole et al. PLCO Project Team (2009) Mortality results from a randomized prostate-cancer screening trial, *N Engl J Med* 360:1310-1319.
4. Schaid et al. Investigators of the International Consortium for Prostate Cancer Genetics (2006) Pooled genome linkage scan of aggressive prostate cancer: Results from the International Consortium for Prostate Cancer Genetics. *Hum Genet* 120:471-485.
5. Lindström et al. (2007) Familial concordance in cancer survival: A Swedish population-based study. *Lancet Oncol* 8:1001-1006.
6. Amundadottir et al. (2006) A common variant associated with prostate cancer in European and African populations. *Nat Genet* 38:652-658.
7. Freedman et al. (2006) Admixture mapping identifies 8q24 as a prostate cancer risk locus in African-American men. *Proc Natl Acad Sci USA* 103:14068-14073.
8. Gudmundsson et al. (2007) Genome-wide association study identifies a second prostate cancer susceptibility variant at 8q24. *Nat Genet* 39:631-637.
9. Yeager et al. (2007) Genome-wide association study of prostate cancer identifies a second risk locus at 8q24. *Nat Genet* 39:645-649.
10. Gudmundsson et al. (2007) Two variants on chromosome 17 confer prostate cancer risk, and the one in TCF2 protects against type 2 diabetes. *Nat Genet* 39:977-983.
11. Thomas et al. (2008) Multiple loci identified in a genome-wide association study of prostate cancer. *Nat Genet* 40:310-315.
12. Gudmundsson et al. (2008) Common sequence variants on 2p15 and Xp11.22 confer susceptibility to prostate cancer. *Nat Genet* 40:281-283.
13. Eeles et al. UK Genetic Prostate Cancer Study Collaborators; British Association of Urological Surgeons' Section of Oncology; UK ProtecT Study Collaborators (2008) Multiple newly identified loci associated with prostate cancer susceptibility. *Nat Genet* 40:316-321.
14. Duggan et al. (2007) Two genome-wide association studies of aggressive prostate cancer implicate putative prostate tumor suppressor gene DAB2IP. *J Natl Cancer Inst* 99:1836-1844.
15. Haiman et al, (2007) Multiple regions within 8q24 independently affect risk for prostate cancer. *Nat Genet* 39:638-644.
16. Zheng et al. (2007) Additive effects of two unlinked loci at 8q24 are associated with a considerable fraction of prostate cancer among European Americans. *J Natl Cancer Inst* 99:1525-1533.
17. Sun et al. (2008) Evidence for two independent prostate cancer risk-associated loci in the HNF1B gene at 17q12. *Nat Genet* 40:1153-1155.
18. Sun et al. (2009) Sequence variants at 22q13 are associated with prostate cancer risk. *Cancer Res* 69:10-15.
19. Chang et al. (2009) Fine mapping association study and functional analysis implicate a SNP in MSMB at 10q11 as a causal variant for prostate cancer risk. *Hum Mol Genet* 18:1368-1375.
20. Hsu et al. (2009) A novel prostate cancer susceptibility locus at 19q13. *Cancer Res* 69:2720-2723.
21. Zheng et al. (2009) Two independent prostate cancer risk-associated loci at 11q13. *Cancer Epidemiol Biomarkers Prev* 18:1815-1820.
22. Yeager et al. (2009) Identification of a new prostate cancer susceptibility locus on chromosome 8q24. *Nat Genet* 41:1055-1057.
23. Gudmundsson et al. (2009) Genome-wide association and replication studies identify four variants associated with prostate cancer susceptibility. *Nat Genet* 41:1122-1126.
24. Eeles et al. UK Genetic Prostate Cancer Study Collaborators/British Association of Urological Surgeons' Section of Oncology; UK ProtecT Study Collaborators; PRACTICAL Consortium (2009) Identification of seven new prostate cancer susceptibility loci through a genome-wide association study. *Nat Genet* 41:1116-1121.
25. Al Olama et al. UK Genetic Prostate Cancer Study Collaborators/British Association of Urological Surgeons' Section of Oncology; UK Prostate testing for cancer and Treatment study (ProtecT Study) Collaborators (2009) Multiple loci on 8q24 associated with prostate cancer susceptibility. *Nat Genet* 41:1058-1060.
26. Kader et al. (2009) Individual and cumulative effect of prostate cancer risk-associated variants on clinicopathologic variables in 5,895 prostate cancer patients. *Prostate* 69:1195-1205.
27. Kote-Jarai et al. PRACTICAL Consortium (2008) Multiple novel prostate cancer predisposition loci confirmed by an international study: The PRACTICAL Consortium. *Cancer Epidemiol Biomarkers Prev* 17:2052-2061.
28. Fitzgerald et al. (2009) Analysis of recently identified prostate cancer susceptibility loci in a population-based study: Associations with family history and clinical features. *Clin Cancer Res* 15:3231-3237.
29. Wiklund et al. (2009) Established prostate cancer susceptibility variants are not associated with disease outcome. *Cancer Epidemiol Biomarkers Prev* 18:1659-1662.
30. Gelmann. (2008) Complexities of prostate-cancer risk. *N Engl J Med* 358:961-963.
31. Witte J S (2009) Prostate cancer genomics: Towards a new understanding. *Nat Rev Genet* 10:77-82.
32. Epstein et al. ISUP Grading Committee (2005) The 2005 International Society of Urological Pathology (ISUP) Consensus Conference on Gleason Grading of Prostatic Carcinoma. *Am J Surg Pathol* 29:1228-1242.
33. Hoedemaeker et al. (2000) Staging prostate cancer. *Microsc Res Tech* 51:423-429.
34. Lotan and Epstein. (2009) Gleason grading of prostatic adenocarcinoma with glomeruloid features on needle biopsy. *Hum Pathol* 40:471-477.
35. Cheng et al. (2008) 8q24 and Prostate cancer: Association with advanced disease and meta-analysis. *Eur J Hum Genet* 16:496-505.
36. Helfand et al. (2008) Tumor characteristics of carriers and noncarriers of the deCODE 8q24 prostate cancer susceptibility alleles, *J Urol*, 179:2197-2201.
37. Kraft and Hunter. (2009) Genetic risk prediction—are we there yet? *N Engl J Med* 360:1701-1703.
38. Cooperberg et al. (2009) Risk assessment for prostate cancer metastasis and mortality at the time of diagnosis. *J Natl Cancer Inst* 101:878-887.
39. Lin. (2004) Functions of heparan sulfate proteoglycans in cell signaling during development. *Development* 131:6009-6021.
40. Stephenson et al. (2009) Prostate cancer-specific mortality after radical prostatectomy for patients treated in the prostate-specific antigen era. *J Clin Oncol* 27:4300-4305.
41. Zheng et al. (2008) Cumulative association of five genetic variants with prostate cancer, *N Engl J Med* 358:910-919.
42. Adolfsson et al. (2007) Clinical characteristics and primary treatment of prostate cancer in Sweden between 1996 and 2005. *Scand J Urol Nephrol* 41:456-477.
43. Stattin et al. National Prostate Cancer Register (2008) Surveillance and deferred treatment for localized prostate cancer. Population based study in the National Prostate Cancer Register of Sweden. *J Urol,* 180:2423-2429.

TABLE 1

Risk Allele Distribution of 183 Aggressive Versus 184 Non-Aggressive
Prostate Cases in a Johns Hopkins Hospital Population

| SNP | CHR | Position | Alleles | Risk allele | Frequency in aggressive prostate cancer | Frequency in non-aggressive prostate cancer | OR |
|---|---|---|---|---|---|---|---|
| rs17641637 | 17 | 12957061 | C/T | T | 0.67 | 0.67 | 1.03 |
| rs11654550 | 17 | 13499770 | T/C | C | 0.59 | 0.56 | 1.15 |
| rs2190856 | 17 | 13502089 | T/G | G | 0.58 | 0.55 | 1.13 |
| rs7215323 | 17 | 13509789 | A/G | A | 0.43 | 0.36 | 1.39 |
| rs7215137 | 17 | 13509982 | A/G | G | 0.59 | 0.58 | 1.06 |
| rs12948596 | 17 | 13511800 | T/C | T | 0.30 | 0.29 | 1.01 |
| rs62056886 | 17 | 13512134 | C/T | T | 0.53 | 0.50 | 1.14 |
| rs62056887 | 17 | 13512555 | A/G | A | 0.23 | 0.21 | 1.13 |
| rs9890022 | 17 | 13516145 | T/C | T | 0.26 | 0.24 | 1.12 |
| rs9892382 | 17 | 13516433 | T/C | C | 0.60 | 0.58 | 1.10 |
| rs58402698 | 17 | 13516645 | G/A | G | 0.26 | 0.24 | 1.14 |
| rs9898581 | 17 | 13517421 | G/C | G | 0.26 | 0.25 | 1.08 |
| rs8077904 | 17 | 13519696 | C/G | G | 0.60 | 0.58 | 1.11 |
| rs9914411 | 17 | 13520722 | G/C | G | 0.22 | 0.21 | 1.06 |
| rs9916271 | 17 | 13520827 | A/T | A | 0.26 | 0.23 | 1.15 |
| rs9895696 | 17 | 13522216 | A/C | A | 0.26 | 0.24 | 1.13 |
| rs9896834 | 17 | 13522666 | C/T | T | 0.60 | 0.58 | 1.12 |
| rs2874922 | 17 | 13523506 | T/C | C | 0.61 | 0.58 | 1.12 |
| rs13342347 | 17 | 13523600 | A/C | A | 0.26 | 0.23 | 1.16 |
| rs13342371 | 17 | 13523675 | T/G | T | 0.26 | 0.23 | 1.16 |
| rs8071527 | 17 | 13523773 | G/A | A | 0.60 | 0.58 | 1.11 |
| rs9899320 | 17 | 13526026 | C/G | C | 0.26 | 0.24 | 1.14 |
| rs55904171 | 17 | 13526981 | C/G | C | 0.26 | 0.24 | 1.14 |
| rs9909795 | 17 | 13527634 | C/T | C | 0.25 | 0.24 | 1.11 |
| rs62056948 | 17 | 13530709 | A/G | A | 0.25 | 0.24 | 1.09 |
| rs55777305 | 17 | 13531676 | G/A | G | 0.30 | 0.29 | 1.01 |
| rs12602893 | 17 | 13534884 | T/G | T | 0.25 | 0.21 | 1.25 |
| rs11078175 | 17 | 13536856 | C/T | T | 0.61 | 0.58 | 1.13 |
| rs62056953 | 17 | 13536977 | G/A | G | 0.26 | 0.23 | 1.15 |
| rs4622548 | 17 | 13538724 | C/T | T | 0.57 | 0.52 | 1.23 |
| rs28824801 | 17 | 13541019 | G/A | G | 0.26 | 0.23 | 1.15 |
| rs12325885 | 17 | 13543663 | T/C | C | 0.60 | 0.57 | 1.11 |
| rs9910556 | 17 | 13544834 | T/C | C | 0.60 | 0.58 | 1.10 |
| rs17588248 | 17 | 13548141 | G/C | G | 0.26 | 0.24 | 1.13 |
| rs11078178 | 17 | 13548190 | A/T | T | 0.60 | 0.58 | 1.11 |
| rs17588297 | 17 | 13548205 | T/C | T | 0.25 | 0.21 | 1.21 |
| rs2874927 | 17 | 13548602 | C/T | C | 0.25 | 0.21 | 1.21 |
| rs8074120 | 17 | 13549576 | A/G | G | 0.60 | 0.58 | 1.10 |
| rs9908002 | 17 | 13549722 | C/T | C | 0.26 | 0.23 | 1.17 |
| rs59486592 | 17 | 13550210 | A/G | A | 0.25 | 0.23 | 1.13 |
| rs4791554 | 17 | 13552900 | G/A | G | 0.25 | 0.22 | 1.20 |
| rs11656731 | 17 | 13552932 | T/A | T | 0.25 | 0.21 | 1.21 |
| rs56662934 | 17 | 13555214 | A/G | A | 0.26 | 0.23 | 1.18 |
| rs12949913 | 17 | 13556021 | G/T | T | 0.59 | 0.57 | 1.07 |
| rs12453942 | 17 | 13560013 | C/G | C | 0.25 | 0.21 | 1.24 |
| rs13353193 | 17 | 13562260 | A/G | A | 0.25 | 0.22 | 1.20 |
| rs9911679 | 17 | 13562733 | G/A | A | 0.78 | 0.73 | 1.34 |
| rs11078179 | 17 | 13563342 | G/T | T | 0.79 | 0.74 | 1.30 |
| rs12942445 | 17 | 13564329 | C/T | T | 0.87 | 0.86 | 1.13 |
| rs12940830 | 17 | 13564583 | G/A | G | 0.19 | 0.16 | 1.17 |
| rs17665271 | 17 | 13564994 | C/T | T | 0.81 | 0.78 | 1.23 |
| rs56216350 | 17 | 13565289 | C/T | T | 0.81 | 0.78 | 1.23 |
| rs16948318 | 17 | 13565430 | A/G | G | 0.78 | 0.73 | 1.35 |
| rs4054823 | 17 | 13565749 | C/T | T | 0.61 | 0.57 | 1.21 |
| rs12942294 | 17 | 13566080 | T/G | G | 0.78 | 0.72 | 1.39 |
| rs12942086 | 17 | 13566150 | T/C | C | 0.78 | 0.73 | 1.38 |

TABLE 2

Number of Patients with More or Less Aggressive Prostate Cancer in Each of Seven Populations

| Study Population | No. of Prostate Cancer Patients | |
|---|---|---|
| | More Aggressive | Less Aggressive |
| CGEMS* | | |
| PLCO | 691 | 489 |
| ACS(CPS-II) | 926 | 699 |
| HPFS | 123 | 405 |
| ATBC | 240 | 516 |
| Subtotal | 1,980 | 2,109 |
| CAPS[†] | 1,231 | 1,619 |
| JHH[‡] | 1,408 | 4,318 |
| PROCAP[§] | 210 | 4,159 |
| Total | 4,829 | 12,205 |

*In the CGEMS study, more aggressive disease is defined as Gleason ≥ 7 or T-stage ≥ T3.
[†]In the CAPS study, more aggressive disease is defined as Gleason ≥ 8 or T-stage ≥ T3.
[‡]In the JHH study, more aggressive disease is defined as Gleason ≥ (4 + 3) or T-stage ≥ T3b or N+.
[§]In the PROCAP study, more aggressive disease is defined as Gleason ≥ 8 or N+.

TABLE 3

Association of SNP rs4054823 at 17p12 with Aggressiveness of PCa

| Study Populations | Genotype Frequency | | | | | | Allele Test Frequency (T) | | Genotype Test | | | | | |
|---|---|---|---|---|---|---|---|---|---|---|---|---|---|---|
| | Aggressive | | | Nonaggressive | | | | | | | Recessive | | Dominant | |
| | CC | CT | TT | CC | CT | TT | Agg | Non-agg | OR(95% CI) | P | OR(95% CI) | P | OR(95% CI) | P |
| CGEMS study | | | | | | | | | | | | | | |
| ACS | 171 | 467 | 275 | 152 | 349 | 183 | 0.56 | 0.52 | 1.15(1.00-1.32) | 0.05 | 1.18(0.95-1.47) | 0.14 | 1.24(0.97-1.58) | 0.09 |
| ATBC | 52 | 119 | 67 | 124 | 253 | 132 | 0.53 | 0.51 | 1.10(0.88-1.37) | 0.39 | 1.12(0.79-1.58) | 0.52 | 1.15(0.80-1.66) | 0.45 |
| HPFS | 29 | 43 | 46 | 75 | 191 | 123 | 0.57 | 0.56 | 1.04(0.78-1.40) | 0.78 | 1.38(0.90-2.12) | 0.14 | 0.73(0.45-1.20) | 0.21 |
| PLCO | 119 | 332 | 233 | 104 | 253 | 126 | 0.58 | 0.52 | 1.28(1.08-1.51) | 3.7E-03 | 1.46(1.13-1.89) | 3.6E-03 | 1.30(0.97-1.75) | 0.08 |
| Sub Total Confirmation | 371 | 961 | 621 | 455 | 1046 | 564 | 0.56 | 0.53 | 1.17(1.06-1.28) | 9.8E-04 | 1.27(1.10-1.47) | 9.1E-04 | 1.18(1.00-1.38) | 0.04 |
| CAPS | 247 | 589 | 387 | 331 | 841 | 428 | 0.56 | 0.52 | 1.11(1.00-1.24) | 0.04 | 1.27(1.08-1.49) | 4.5E-03 | 1.03(0.86-1.24) | 0.75 |
| JHH | 289 | 662 | 448 | 912 | 2152 | 1217 | 0.56 | 0.54 | 1.09(1.00-1.19) | 0.05 | 1.19(1.04-1.35) | 1.0E-02 | 1.04(0.90-1.21) | 0.61 |
| PROCAP | 35 | 93 | 81 | 853 | 2079 | 1215 | 0.61 | 0.54 | 1.31(1.07-1.61) | 0.01 | 1.53(1.15-2.03) | 3.5E-03 | 1.29(0.89-1.87) | 0.18 |
| Sub Total | 571 | 1344 | 916 | 2096 | 5072 | 2860 | 0.56 | 0.54 | 1.12(1.05-1.19) | 5.0E-04 | 1.25(1.13-1.37) | 6.2E-06 | 1.06(0.95-1.18) | 0.32 |
| All Populations | 942 | 2305 | 1537 | 2551 | 6118 | 3424 | 0.56 | 0.54 | 1.13(1.08-1.19) | 2.1E-06 | 1.26(1.16-1.36) | 2.1E-08 | 1.09(1.00-1.20) | 0.05 |

Recessive and dominant models are defined in terms of risk allele T. For Subtotal and All Populations, the P value or OR (95% CI) were calculated from the CMH test. Breslow-Day P value for all populations/recessive mode is 0.5646.

TABLE 4

Clinical and Demographic Characteristics of Subjects in CAPS

| Characteristic | No. (%) of cases | | | No. (%) of controls (n = 1,722) |
|---|---|---|---|---|
| | Aggressive (n = 1,231) | Localized (n = 1,619) | All cases (n = 2,899) | |
| Age at enrollment (y) | | | | |
| Mean (SD) | 68.04 (7.32) | 65.14 (6.74) | 66.36 (7.13) | 67.15 (7.39) |
| Age, y, at diagnosis | | | | |
| 65 | 514 (41.75) | 926 (57.19) | 1469 (50.78) | N/A |
| >65 | 717 (58.25) | 693 (42.81) | 1424 (49.22) | N/A |
| Family history (first-degree relatives) | | | | |
| No | 1013 (82.29) | 1295 (79.99) | 2,342 (80.95) | 1,565 (90.57) |
| Yes | 218 (17.71) | 324 (20.01) | 551 (19.05) | 163 (9.43) |
| Missing data | 0 | 0 | 0 | 0 |
| PSA levels at diagnosis for cases or at enrollment for controls (ng/mL) | | | | |
| 4 | 36 (2.95) | 185 (11.61) | 221 (7.85) | 1,438 (83.56) |
| 4.01-9.99 | 171 (14.00) | 755 (47.39) | 926 (32.91) | 230 (13.36) |
| 10-19.99 | 216 (17.69) | 438 (27.50) | 654 (23.24) | 37 (2.15) |
| 20-49.99 | 252 (20.64) | 215 (13.50) | 467 (16.60) | 13 (0.76) |

TABLE 4-continued

Clinical and Demographic Characteristics of Subjects in CAPS

| Characteristic | No. (%) of cases | | | No. (%) of controls (n = 1,722) |
|---|---|---|---|---|
| | Aggressive (n = 1,231) | Localized (n = 1,619) | All cases (n = 2,899) | |
| 50-99.99 | 229 (18.76) | 0 | 229 (8.14) | 2 (0.12) |
| 100 | 317 (25.96) | 0 | 317 (11.27) | 1 (0.06) |
| Missing | 10 | 26 | 85 | 1 |
| T-stage | | | | |
| T0 | 2 (0.16) | 7 (0.44) | 9 (0.32) | N/A |
| T1 | 147 (12.07) | 933 (58.24) | 1080 (38.30) | N/A |
| T2 | 242 (19.87) | 662 (41.32) | 904 (32.06) | N/A |
| T3 | 724 (59.44) | 0 | 724 (25.67) | N/A |
| T4 | 103 (8.46) | 0 | 103 (3.65) | N/A |
| TX | 13 | 17 | 79 | N/A |
| N-stage | | | | |
| N0 | 222 (70.03) | 302 (100.00) | 524 (84.65) | N/A |
| N1 | 95 (29.97) | 0 | 95 (15.35) | N/A |
| NX | 914 | 1317 | 2280 | N/A |
| M-stage | | | | |
| M0 | 589 (68.25) | 655 (100.00) | 1244 (81.95) | N/A |
| M1 | 274 (31.75) | 0 | 274 (18.05) | N/A |
| MX | 368 | 964 | 1381 | N/A |
| Gleason (biopsy) | | | | |
| 4 | 9 (0.83) | 98 (6.32) | 107 (4.06) | N/A |
| 5 | 43 (3.96) | 247 (15.93) | 290 (10.99) | N/A |
| 6 | 153 (14.08) | 832 (53.64) | 985 (37.34) | N/A |
| 7 | 414 (38.09) | 374 (24.11) | 788 (29.87) | N/A |
| 8 | 258 (23.74) | 0 | 258 (9.78) | N/A |
| 9 | 185 (17.02) | 0 | 185 (7.01) | N/A |
| 10 | 25 (2.30) | 0 | 25 | N/A |
| Missing | 144 | 68 | 261 | N/A |

Forty-nine patients could not be classified as having aggressive or localized disease because of missing phenotypes.

TABLE 5

Clinical and Demographic Characteristics of Study Subjects

| Characteristic | No. (%) of cases | | | Controls (n = 482) |
|---|---|---|---|---|
| | Aggressive (n = 1,408) | Indolent (n = 4,318) | All cases (n = 5,955) | |
| Age at enrollment (y) | | | | |
| Mean (SD) | 59.8 (6.72) | 57.7 (6.49) | 58.3 (6.69) | 59.91 (7.19) |
| Age at diagnosis (y) | | | | |
| ≤65 | 1,112 (78.98) | 3,833 (88.77) | 5,115 (85.89) | |
| >65 | 296 (21.02) | 485 (11.23) | 839 (14.09) | |
| PSA levels at diagnosis for cases or at enrollment for controls (ng/mL) | | | | |
| ≤4 | 139 (9.87) | 1,095 (25.36) | 1,262 (21.19) | 481 (99.79) |
| 4.01-9.99 | 611 (43.39) | 2,264 (52.43) | 2,951 (49.55) | 0 |
| 10-19.99 | 182 (12.93) | 247 (5.72) | 451 (7.57) | 0 |
| 20-49.99 | 84 (5.97) | 36 (0.83) | 131 (2.2) | 0 |
| 50-99.99 | 34 (2.41) | 4 (0.09) | 58 (0.97) | 0 |
| ≥100 | 63 (4.47) | 3 (0.07) | 117 (1.96) | 0 |
| Missing | 196 (13.92) | 669 (15.49) | 985 (16.54) | 1 (0.21) |
| T-stage | | | | |
| T0 | NA | NA | NA | NA |
| T1 | NA | NA | NA | NA |
| T2 | 368 (26.14) | 3,416 (79.11) | 3,850 (64.65) | NA |
| T3a | 536 (38.07) | 902 (20.89) | 1,454 (24.42) | NA |
| T3b/c | 355 (25.21) | 0 | 355 (5.96) | NA |
| T3/T3X | 9 (0.64) | 0 | 15 (0.25) | NA |
| T4 | 3 (0.21) | 0 | 3 (0.05) | NA |
| TX | 137 (9.73) | 0 | 278 (4.67) | NA |

TABLE 5-continued

Clinical and Demographic Characteristics of Study Subjects

| | No. (%) of cases | | | |
|---|---|---|---|---|
| Characteristic | Aggressive (n = 1,408) | Indolent (n = 4,318) | All cases (n = 5,955) | Controls (n = 482) |
| N-stage | | | | |
| N0 | 1,085 (77.06) | 4,318 (100) | 5,469 (91.84) | NA |
| N1 | 140 (9.94) | 0 (0) | 140 (2.35) | NA |
| NX | 183 (13) | 0 (0) | 346 (5.81) | NA |
| M-stage | | | | |
| M0 | NA | NA | NA | NA |
| M1 | NA | NA | NA | NA |
| MX | 1,408 | 4,318 | 5,955 | NA |
| Gleason score (biopsy) | | | | |
| ≤4 | 0 | 0 | 2 (0.03) | NA |
| 5 | 2 (0.14) | 67 (1.55) | 73 (1.23) | NA |
| 6 | 23 (1.63) | 3,042 (70.45) | 3,104 (52.12) | NA |
| 7 (3 + 4) | 106 (7.53) | 1,254 (29.04) | 1,411 (23.69) | NA |
| 7 (4 + 3) | 667 (47.37) | 0 | 667 (11.2) | NA |
| 8 | 317 (22.51) | 0 | 317 (5.32) | NA |
| 9 | 265 (18.82) | 0 | 265 (4.45) | NA |
| 10 | 18 (1.28) | 0 | 18 (0.3) | NA |
| Missing | 10 (0.71) | 0 | 98 (1.65) | NA |

A total of 229 patients could not be classified as having aggressive or indolent disease because of missing phenotypes.

TABLE 6

Genotype Frequency of SNP rs4054823 at 17p12 in Controls as Well as Case Patients With Aggressive or Indolent Disease

| | | Genotype frequency | | | Genotype test (recessive model for T) | | | Controls vs. aggressive | |
|---|---|---|---|---|---|---|---|---|---|
| | | | | | Controls | | | | |
| | Study population | Aggressive | | | Indolent | | | | |
| | | CC | CT | TT | CC | CT | TT | CC | CT |
| CGEMS study | | | | | | | | | |
| ACS | 339 | 904 | 532 | 171 | 467 | 275 | 152 | 349 | 183 |
| ATBC | 228 | 473 | 219 | 52 | 119 | 67 | 124 | 253 | 132 |
| HPFS | 126 | 304 | 181 | 29 | 43 | 46 | 75 | 191 | 123 |
| PLCO | 226 | 548 | 319 | 119 | 332 | 233 | 104 | 253 | 126 |
| Sub total | 919 | 2,229 | 1,251 | 371 | 961 | 621 | 455 | 1,046 | 564 |
| Confirmation | | | | | | | | | |
| CAPS | 362 | 865 | 484 | 247 | 589 | 387 | 331 | 841 | 428 |
| JHH | 106 | 234 | 140 | 289 | 662 | 448 | 912 | 2,152 | 1,217 |
| Sub total | 468 | 1,099 | 624 | 536 | 1,251 | 835 | 1,243 | 2,993 | 1,645 |
| All populations | 1,387 | 3,328 | 1,875 | 907 | 2,212 | 1,456 | 1,698 | 4,039 | 2,209 |

| | Controls | | Controls vs. indolent | |
|---|---|---|---|---|
| | TT | OR (95% CI) | P | OR (95% CI) P |
| CGEMS study | | | | |
| ACS | 1.01 (0.85-1.20) | 0.937 | 0.85 (0.70-1.04) | 0.116 |
| ATBC | 1.25 (0.91-1.73) | 0.166 | 1.12 (0.87-1.44) | 0.371 |
| HPFS | 1.52 (1.01-2.28) | 0.045 | 1.10 (0.83-1.45) | 0.504 |
| PLCO | 1.25 (1.02-1.54) | 0.031 | 0.86 (0.67-1.09) | 0.208 |
| Sub total | 1.15 (1.02-1.29) | 0.019 | 0.95 (0.84-1.08) | 0.386 |

TABLE 6-continued

Genotype Frequency of SNP rs4054823 at 17p12 in Controls as
Well as Case Patients With Aggressive or Indolent Disease

| | Confirmation | | | | |
|---|---|---|---|---|---|
| | CAPS | 1.17 (1.00-1.37) | 0.050 | 0.93 (0.79-1.08) | 0.322 |
| | JHH | 1.14 (0.91-1.44) | 0.244 | 0.96 (0.78-1.19) | 0.734 |
| | Sub total | 1.16 (1.02-1.33) | 0.023 | 0.94 (0.83-1.06) | 0.318 |
| | All populations | 1.16 (1.06-1.26) | 1.1E−03 | 0.94 (0.87-1.03) | 0.188 |

P value and OR (95% CI) in combined populations are for the CMH test. In Controls vs. Aggressive, the Breslow-Day P value for all populations is 0.4142.

TABLE 7

Confirmation of SNPs Associated With Aggressiveness of Prostate Cancer in CAPS

| | | | | CGEMS, 1st stage | | | CGESM, 2nd stage | | | | | |
|---|---|---|---|---|---|---|---|---|---|---|---|---|
| dbSNP ID | Chromosome | Physical Position (bp) | Allele | Aggressive-PLCO, n = 691 | indolent-PLCO, n = 489 | P-PLCO | Aggressive-ACS, n = 926 | indolent-ACS, n = 699 | P-ACS | Aggressive-ATBC, n = 240 | indolent-ATBC, n = 516 | P-ATBC |
| rs9438989 | 1 | 39,041,936 | G | 0.24 | 0.2 | 0.0419 | 0.25 | 0.24 | 0.7291 | 0.24 | 0.2 | 0.0949 |
| rs4950142 | 1 | 98,253,698 | C | 0.23 | 0.27 | 0.0162 | 0.23 | 0.27 | 0.013 | 0.16 | 0.17 | 0.6353 |
| rs603246 | 1 | 166,624,862 | G | 0.45 | 0.41 | 0.0343 | 0.47 | 0.44 | 0.1138 | 0.51 | 0.45 | 0.0371 |
| rs288324 | 2 | 183,527,094 | A | 0.48 | 0.43 | 0.0398 | 0.5 | 0.44 | 0.0012 | 0.51 | 0.48 | 0.1575 |
| rs2049716 | 2 | 184,291,156 | A | 0.17 | 0.21 | 0.0344 | 0.19 | 0.22 | 0.0537 | 0.16 | 0.18 | 0.3384 |
| rs6738940 | 2 | 208,868,469 | G | 0.17 | 0.21 | 0.0185 | 0.15 | 0.18 | 0.039 | 0.14 | 0.18 | 0.0914 |
| rs7631088 | 3 | 1,054,024 | G | 0.48 | 0.52 | 0.0435 | 0.49 | 0.51 | 0.2277 | 0.5 | 0.51 | 0.6716 |
| rs12490386 | 3 | 4,021,849 | A | 0.15 | 0.12 | 0.0175 | 0.13 | 0.12 | 0.2911 | 0.11 | 0.08 | 0.0284 |
| rs12632229 | 3 | 72,722,484 | G | 0.43 | 0.37 | 0.007 | 0.43 | 0.4 | 0.0959 | 0.47 | 0.41 | 0.0425 |
| rs7639273 | 3 | 108,211,376 | G | 0.17 | 0.13 | 0.0066 | 0.15 | 0.13 | 0.0793 | 0.1 | 0.08 | 0.2189 |
| rs1515577 | 3 | 121,611,630 | T | 0.49 | 0.45 | 0.0495 | 0.51 | 0.48 | 0.1016 | 0.5 | 0.46 | 0.1091 |
| rs6772915 | 3 | 125,553,929 | G | 0.4 | 0.33 | 0.0019 | 0.36 | 0.34 | 0.1099 | 0.46 | 0.45 | 0.5306 |
| rs9825812 | 3 | 127,505,666 | T | 0.45 | 0.5 | 0.0301 | 0.46 | 0.47 | 0.631 | 0.4 | 0.46 | 0.0152 |
| rs12629405 | 3 | 169,834,562 | A | 0.48 | 0.44 | 0.0418 | 0.47 | 0.44 | 0.0981 | 0.65 | 0.61 | 0.2214 |
| rs9996597 | 4 | 111,652 | T | 0.49 | 0.45 | 0.0484 | 0.46 | 0.41 | 0.0048 | 0.56 | 0.54 | 0.5724 |
| rs734526 | 4 | 7,715,523 | C | 0.37 | 0.32 | 0.0077 | 0.35 | 0.31 | 0.0373 | 0.41 | 0.38 | 0.3496 |
| rs17579878 | 4 | 114,423,937 | A | 0.16 | 0.2 | 0.0196 | 0.17 | 0.2 | 0.1115 | 0.17 | 0.19 | 0.3694 |
| rs13128882 | 4 | 116,569,315 | A | 0.38 | 0.34 | 0.0446 | 0.38 | 0.37 | 0.3915 | 0.38 | 0.34 | 0.218 |
| rs4582131 | 4 | 153,582,583 | T | 0.11 | 0.08 | 0.0236 | 0.09 | 0.08 | 0.1443 | 0.09 | 0.06 | 0.0991 |
| rs11132055 | 4 | 182,697,954 | G | 0.11 | 0.15 | 0.004 | 0.13 | 0.14 | 0.2089 | 0.09 | 0.11 | 0.2157 |
| rs16903125 | 5 | 34,618,895 | C | 0.12 | 0.08 | 0.0026 | 0.11 | 0.08 | 0.034 | 0.11 | 0.09 | 0.0949 |
| rs6451722 | 5 | 43,747,135 | G | 0.19 | 0.24 | 0.0048 | 0.2 | 0.24 | 0.0043 | 0.15 | 0.16 | 0.5206 |
| rs159574 | 5 | 55,515,419 | T | 0.39 | 0.34 | 0.0327 | 0.39 | 0.37 | 0.2688 | 0.36 | 0.35 | 0.5547 |
| rs1826692 | 5 | 116,652,980 | A | 0.33 | 0.37 | 0.0478 | 0.35 | 0.38 | 0.1222 | 0.29 | 0.33 | 0.0818 |
| rs249888 | 5 | 155,599,372 | C | 0.33 | 0.25 | 5E−05 | 0.3 | 0.28 | 0.1577 | 0.34 | 0.31 | 0.2177 |
| rs4704998 | 5 | 155,613,992 | A | 0.26 | 0.21 | 0.0055 | 0.24 | 0.23 | 0.2442 | 0.29 | 0.25 | 0.0702 |
| rs12194118 | 6 | 4,272,255 | T | 0.44 | 0.49 | 0.0143 | 0.47 | 0.51 | 0.0079 | 0.43 | 0.46 | 0.4056 |
| rs2806371 | 6 | 109,328,539 | A | 0.4 | 0.45 | 0.0209 | 0.42 | 0.43 | 0.3709 | 0.31 | 0.38 | 0.0052 |
| rs886505 | 7 | 8,559,297 | A | 0.43 | 0.5 | 0.0004 | 0.46 | 0.49 | 0.0753 | 0.56 | 0.61 | 0.1162 |
| rs2713328 | 7 | 9,260,649 | A | 0.18 | 0.13 | 0.0006 | 0.17 | 0.14 | 0.0121 | 0.22 | 0.2 | 0.393 |
| rs1229655 | 7 | 26,206,164 | C | 0.27 | 0.23 | 0.0374 | 0.26 | 0.24 | 0.1598 | 0.17 | 0.15 | 0.3239 |
| rs2391671 | 7 | 28,325,617 | A | 0.29 | 0.24 | 0.0267 | 0.27 | 0.24 | 0.0924 | 0.29 | 0.26 | 0.2283 |
| rs2726005 | 7 | 85,205,173 | G | 0.16 | 0.12 | 0.0084 | 0.15 | 0.14 | 0.5543 | 0.16 | 0.13 | 0.2501 |
| rs1487745 | 8 | 18,665,612 | G | 0.09 | 0.13 | 0.0015 | 0.09 | 0.11 | 0.3302 | 0.12 | 0.14 | 0.2257 |
| rs6472429 | 8 | 70,000,821 | C | 0.51 | 0.46 | 0.0181 | 0.51 | 0.48 | 0.0805 | 0.53 | 0.5 | 0.3454 |
| rs7011777 | 8 | 124,036,356 | T | 0.25 | 0.2 | 0.0192 | 0.26 | 0.22 | 0.007 | 0.21 | 0.19 | 0.5165 |
| rs11994203 | 8 | 125,672,479 | G | 0.18 | 0.13 | 0.0022 | 0.17 | 0.14 | 0.054 | 0.29 | 0.25 | 0.1431 |
| rs13293601 | 9 | 12,897,902 | C | 0.18 | 0.22 | 0.0231 | 0.17 | 0.2 | 0.0322 | 0.17 | 0.19 | 0.5315 |
| rs10217763 | 9 | 22,588,914 | A | 0.19 | 0.22 | 0.0307 | 0.19 | 0.23 | 0.0285 | 0.17 | 0.2 | 0.1655 |
| rs11139934 | 9 | 83,009,358 | A | 0.23 | 0.19 | 0.0168 | 0.24 | 0.22 | 0.2442 | 0.19 | 0.15 | 0.0881 |
| rs1875411 | 9 | 106,824,524 | A | 0.13 | 0.1 | 0.0163 | 0.13 | 0.1 | 0.0349 | 0.08 | 0.06 | 0.1918 |
| rs1871692 | 9 | 113,580,831 | T | 0.27 | 0.31 | 0.0317 | 0.27 | 0.3 | 0.0648 | 0.34 | 0.36 | 0.5993 |
| rs7909593 | 10 | 12,442,472 | A | 0.08 | 0.11 | 0.0228 | 0.1 | 0.12 | 0.0819 | 0.11 | 0.12 | 0.4424 |
| rs2148308 | 10 | 21,092,954 | A | 0.46 | 0.4 | 0.0124 | 0.46 | 0.44 | 0.2321 | 0.4 | 0.35 | 0.0635 |
| rs7907961 | 10 | 44,051,001 | T | 0.25 | 0.2 | 0.0092 | 0.25 | 0.23 | 0.3796 | 0.31 | 0.24 | 0.0053 |
| rs9416489 | 10 | 57,531,487 | G | 0.46 | 0.51 | 0.0088 | 0.47 | 0.51 | 0.037 | 0.49 | 0.55 | 0.0394 |
| rs7917290 | 10 | 71,536,167 | T | 0.17 | 0.13 | 0.0117 | 0.16 | 0.14 | 0.1974 | 0.22 | 0.19 | 0.1301 |
| rs10831706 | 11 | 2,262,602 | A | 0.07 | 0.11 | 0.0036 | 0.11 | 0.13 | 0.1804 | 0.1 | 0.12 | 0.1424 |
| rs7114018 | 11 | 8,046,522 | C | 0.4 | 0.46 | 0.0045 | 0.44 | 0.47 | 0.0871 | 0.35 | 0.41 | 0.0359 |
| rs12576547 | 11 | 10,599,800 | C | 0.38 | 0.43 | 0.0204 | 0.41 | 0.44 | 0.1078 | 0.39 | 0.42 | 0.3764 |
| rs4077215 | 11 | 11,530,606 | T | 0.4 | 0.36 | 0.0467 | 0.44 | 0.4 | 0.0465 | 0.3 | 0.28 | 0.4531 |
| rs10837311 | 11 | 39,938,524 | G | 0.19 | 0.23 | 0.011 | 0.19 | 0.23 | 0.0208 | 0.11 | 0.15 | 0.0811 |
| rs1320722 | 11 | 79,156,374 | T | 0.36 | 0.41 | 0.0117 | 0.35 | 0.39 | 0.0312 | 0.44 | 0.44 | 0.9498 |
| rs6589849 | 11 | 98,391,541 | C | 0.25 | 0.3 | 0.0119 | 0.26 | 0.29 | 0.0463 | 0.25 | 0.32 | 0.0059 |
| rs1105721 | 11 | 130,573,660 | C | 0.37 | 0.32 | 0.0228 | 0.34 | 0.31 | 0.0919 | 0.41 | 0.37 | 0.1946 |

TABLE 7-continued

Confirmation of SNPs Associated With Aggressiveness of Prostate Cancer in CAPS

| rs16919663 | 12 | 32,345,199 | A | 0.16 | 0.13 | 0.0472 | 0.15 | 0.13 | 0.0471 | 0.21 | 0.19 | 0.3358 |
|---|---|---|---|---|---|---|---|---|---|---|---|---|
| rs10861272 | 12 | 103,613,005 | A | 0.08 | 0.11 | 0.0118 | 0.11 | 0.13 | 0.053 | 0.09 | 0.12 | 0.0973 |
| rs9513353 | 13 | 97,548,317 | A | 0.18 | 0.13 | 0.002 | 0.18 | 0.15 | 0.0271 | 0.21 | 0.2 | 0.442 |
| rs9300549 | 13 | 98,901,735 | A | 0.41 | 0.36 | 0.0122 | 0.39 | 0.35 | 0.0358 | 0.44 | 0.41 | 0.2989 |
| rs4773194 | 13 | 109,930,491 | G | 0.21 | 0.18 | 0.0279 | 0.2 | 0.17 | 0.0203 | 0.16 | 0.15 | 0.6374 |
| rs7999702 | 13 | 110,180,265 | T | 0.18 | 0.22 | 0.0227 | 0.18 | 0.2 | 0.1121 | 0.27 | 0.29 | 0.4378 |
| rs914009 | 14 | 55,876,855 | G | 0.37 | 0.32 | 0.0078 | 0.35 | 0.32 | 0.0276 | 0.35 | 0.32 | 0.1759 |
| rs2921452 | 14 | 76,010,170 | G | 0.51 | 0.47 | 0.0288 | 0.47 | 0.45 | 0.1194 | 0.51 | 0.46 | 0.1153 |
| rs12438353 | 15 | 85,116,084 | C | 0.3 | 0.35 | 0.0196 | 0.3 | 0.33 | 0.1494 | 0.4 | 0.44 | 0.2058 |
| rs11247363 | 15 | 96,441,465 | C | 0.43 | 0.49 | 0.007 | 0.45 | 0.48 | 0.1617 | 0.47 | 0.54 | 0.0143 |
| rs4054823 | 17 | 13,565,749 | T | 0.42 | 0.48 | 0.0037 | 0.44 | 0.48 | 0.0542 | 0.47 | 0.49 | 0.394 |
| rs972317 | 17 | 31,395,772 | A | 0.12 | 0.09 | 0.0329 | 0.13 | 0.1 | 0.0336 | 0.16 | 0.16 | 0.9916 |
| rs12150382 | 17 | 65,734,367 | G | 0.24 | 0.29 | 0.0112 | 0.22 | 0.26 | 0.0175 | 0.19 | 0.23 | 0.0957 |
| rs1790588 | 18 | 65,686,164 | T | 0.47 | 0.42 | 0.0341 | 0.49 | 0.45 | 0.0223 | 0.49 | 0.44 | 0.1178 |
| rs2306199 | 19 | 8,226,890 | T | 0.38 | 0.45 | 0.0009 | 0.38 | 0.41 | 0.0847 | 0.22 | 0.24 | 0.4226 |
| rs2288888 | 19 | 43,638,022 | A | 0.33 | 0.28 | 0.0147 | 0.35 | 0.3 | 0.0083 | 0.36 | 0.3 | 0.0227 |
| rs5992590 | 22 | 15,787,360 | T | 0.25 | 0.3 | 0.0099 | 0.27 | 0.3 | 0.043 | 0.32 | 0.33 | 0.7308 |
| rs2091051 | 22 | 47,933,870 | C | 0.41 | 0.45 | 0.023 | 0.42 | 0.44 | 0.1981 | 0.51 | 0.57 | 0.0498 |
| rs6010061 | 22 | 49,441,868 | C | 0.43 | 0.36 | 0.0022 | 0.4 | 0.38 | 0.1209 | 0.6 | 0.57 | 0.3278 |

| | CGESM, 2nd stage | | | | | CAPS | | | | |
|---|---|---|---|---|---|---|---|---|---|---|
| | Aggressive- HPFS, n = 123 | indolent- HTFS, n = 405 | P-HPFS | CGEMS P-CMH | Rank | Allele | Aggressive, n = 1,231 | indolent, n = 1,619 | P | OR |
| dbSNP ID | | | | | | | | | | |
| rs9438989 | 0.33 | 0.24 | 0.0084 | 0.0041 | 237 | T | 0.24 | 0.24 | 0.8664 | 0.99 |
| rs4950142 | 0.24 | 0.24 | 0.9814 | 0.0014 | 103 | T | 0.22 | 0.23 | 0.3348 | 0.94 |
| rs603246 | 0.44 | 0.42 | 0.6606 | 0.0013 | 100 | A | 0.45 | 0.45 | 0.7575 | 1.02 |
| rs288324 | 0.52 | 0.46 | 0.144 | 2E−05 | 3 | C | 0.48 | 0.49 | 0.1625 | 0.93 |
| rs2049716 | 0.18 | 0.21 | 0.4185 | 0.0021 | 139 | C | 0.19 | 0.19 | 0.6158 | 0.97 |
| rs6738940 | 0.17 | 0.17 | 0.8912 | 0.0007 | 61 | A | 0.16 | 0.16 | 0.6966 | 0.97 |
| rs7631088 | 0.43 | 0.53 | 0.0097 | 0.0039 | 226 | A | 0.49 | 0.48 | 0.6587 | 1.02 |
| rs12490386 | 0.15 | 0.11 | 0.2046 | 0.0011 | 91 | G | 0.14 | 0.14 | 0.3879 | 0.94 |
| rs12632229 | 0.41 | 0.4 | 0.7841 | 0.0005 | 39 | A | 0.42 | 0.42 | 0.7796 | 0.98 |
| rs7639273 | 0.14 | 0.14 | 0.7321 | 0.0011 | 87 | T | 0.11 | 0.12 | 0.1717 | 0.89 |
| rs1515577 | 0.54 | 0.47 | 0.0524 | 0.0006 | 53 | C | 0.48 | 0.48 | 0.7894 | 0.99 |
| rs6772915 | 0.37 | 0.31 | 0.0586 | 0.0003 | 29 | T | 0.4 | 0.39 | 0.3406 | 1.05 |
| rs9825812 | 0.45 | 0.52 | 0.0746 | 0.0021 | 135 | C | 0.46 | 0.44 | 0.2024 | 1.07 |
| rs12629405 | 0.52 | 0.44 | 0.0427 | 0.0008 | 68 | A | 0.47 | 0.49 | 0.2336 | 0.94 |
| rs9996597 | 0.46 | 0.42 | 0.2754 | 0.0005 | 41 | T | 0.47 | 0.51 | 0.01694 | 0.88 |
| rs734526 | 0.39 | 0.34 | 0.1409 | 0.0002 | 21 | T | 0.36 | 0.35 | 0.496 | 1.04 |
| rs17579878 | 0.14 | 0.16 | 0.2791 | 0.0024 | 158 | G | 0.19 | 0.18 | 0.2943 | 1.08 |
| rs13128882 | 0.43 | 0.36 | 0.0443 | 0.005 | 291 | G | 0.39 | 0.39 | 0.8024 | 1.01 |
| rs4582131 | 0.12 | 0.1 | 0.3849 | 0.0016 | 111 | C | 0.09 | 0.09 | 0.8448 | 1.02 |
| rs11132055 | 0.1 | 0.13 | 0.2363 | 0.001 | 82 | T | 0.1 | 0.11 | 0.394 | 0.93 |
| rs16903125 | 0.12 | 0.1 | 0.4187 | 6E−05 | 7 | A | 0.01 | 0.01 | 0.9583 | 0.98 |
| rs6451722 | 0.21 | 0.23 | 0.6136 | 0.0001 | 12 | A | 0.19 | 0.19 | 0.6309 | 1.03 |
| rs159574 | 0.47 | 0.39 | 0.0298 | 0.0046 | 266 | C | 0.39 | 0.39 | 0.7228 | 1.02 |
| rs1826692 | 0.36 | 0.38 | 0.6221 | 0.003 | 185 | C | 0.35 | 0.34 | 0.8512 | 1.01 |
| rs249888 | 0.33 | 0.3 | 0.3151 | 7E−05 | 8 | T | 0.29 | 0.28 | 0.4397 | 1.05 |
| rs4704998 | 0.27 | 0.23 | 0.2257 | 0.0006 | 51 | G | 0.24 | 0.23 | 0.4429 | 1.05 |
| rs12194118 | 0.5 | 0.52 | 0.628 | 0.0003 | 30 | G | 0.45 | 0.45 | 0.7227 | 1.02 |
| rs2806371 | 0.39 | 0.43 | 0.3759 | 0.001 | 83 | G | 0.42 | 0.42 | 0.7459 | 0.98 |
| rs886505 | 0.48 | 0.48 | 0.9553 | 0.0002 | 18 | G | 0.44 | 0.48 | 0.00173 | 0.84 |
| rs2713328 | 0.15 | 0.14 | 0.8403 | 9E−05 | 9 | C | 0.2 | 0.16 | 0.00208 | 1.24 |
| rs1229655 | 0.29 | 0.22 | 0.0303 | 0.0015 | 108 | T | 0.24 | 0.22 | 0.267 | 1.07 |
| rs2391671 | 0.27 | 0.25 | 0.5863 | 0.0027 | 171 | G | 0.27 | 0.25 | 0.2224 | 1.08 |
| rs2726005 | 0.22 | 0.13 | 0.0005 | 0.0006 | 55 | A | 0.15 | 0.14 | 0.5121 | 1.05 |
| rs1487745 | 0.06 | 0.1 | 0.0695 | 0.0005 | 49 | A | 0.1 | 0.11 | 0.5837 | 0.95 |
| rs6472429 | 0.55 | 0.48 | 0.082 | 0.0007 | 63 | C | 0.49 | 0.5 | 0.2985 | 0.95 |
| rs7011777 | 0.25 | 0.24 | 0.9771 | 0.0008 | 70 | C | 0.25 | 0.24 | 0.3082 | 1.07 |
| rs11994203 | 0.19 | 0.16 | 0.2253 | 9E−05 | 11 | T | 0.22 | 0.21 | 0.7452 | 1.02 |
| rs13293601 | 0.16 | 0.18 | 0.4539 | 0.0016 | 115 | A | 0.18 | 0.2 | 0.1581 | 0.91 |
| rs10217763 | 0.21 | 0.21 | 0.8174 | 0.0011 | 90 | G | 0.2 | 0.22 | 0.04108 | 0.87 |
| rs11139934 | 0.27 | 0.2 | 0.0236 | 0.0005 | 48 | G | 0.2 | 0.2 | 0.83 | 0.99 |
| rs1875411 | 0.11 | 0.11 | 0.8351 | 0.0009 | 76 | G | 0.1 | 0.1 | 0.5589 | 1.05 |
| rs1871692 | 0.25 | 0.28 | 0.447 | 0.0047 | 271 | C | 0.29 | 0.3 | 0.4047 | 0.95 |
| rs7909593 | 0.09 | 0.12 | 0.1472 | 0.0017 | 118 | C | 0.12 | 0.12 | 0.5741 | 0.95 |
| rs2148308 | 0.5 | 0.43 | 0.0425 | 0.0004 | 33 | C | 0.39 | 0.42 | 0.04485 | 0.9 |
| rs7907961 | 0.29 | 0.21 | 0.0074 | 6E−05 | 6 | C | 0.25 | 0.25 | 0.6056 | 1.03 |
| rs9416489 | 0.46 | 0.48 | 0.7116 | 0.0002 | 17 | G | 0.49 | 0.5 | 0.8346 | 0.99 |
| rs7917290 | 0.19 | 0.18 | 0.5209 | 0.0022 | 147 | G | 0.18 | 0.18 | 0.8748 | 0.99 |
| rs10831706 | 0.11 | 0.12 | 0.4926 | 0.0013 | 98 | G | 0.09 | 0.09 | 0.5637 | 0.95 |
| rs7114018 | 0.4 | 0.43 | 0.466 | 0.0002 | 15 | T | 0.42 | 0.42 | 0.9301 | 1 |

TABLE 7-continued

Confirmation of SNPs Associated With Aggressiveness of Prostate Cancer in CAPS

| | | | | | | | | | | |
|---|---|---|---|---|---|---|---|---|---|---|
| rs12576547 | 0.39 | 0.41 | 0.4594 | 0.0034 | 209 | A | 0.44 | 0.43 | 0.8446 | 1.01 |
| rs4077215 | 0.4 | 0.39 | 0.6602 | 0.0043 | 247 | G | 0.32 | 0.33 | 0.3188 | 0.94 |
| rs10837311 | 0.19 | 0.21 | 0.6019 | 0.0002 | 16 | A | 0.18 | 0.17 | 0.924 | 1.01 |
| rs1320722 | 0.35 | 0.37 | 0.4639 | 0.0024 | 156 | C | 0.41 | 0.44 | 0.0316 | 0.89 |
| rs6589849 | 0.25 | 0.26 | 0.8373 | 9E−05 | 10 | A | 0.26 | 0.27 | 0.373 | 0.95 |
| rs1105721 | 0.34 | 0.33 | 0.7764 | 0.0028 | 176 | A | 0.35 | 0.33 | 0.2058 | 1.07 |
| rs16919663 | 0.14 | 0.13 | 0.6937 | 0.0037 | 219 | C | 0.16 | 0.15 | 0.5395 | 1.05 |
| rs10861272 | 0.08 | 0.12 | 0.0847 | 0.0001 | 13 | G | 0.01 | 0.01 | 0.7437 | 0.92 |
| rs9513353 | 0.17 | 0.15 | 0.4432 | 0.0002 | 22 | G | 0.14 | 0.15 | 0.6093 | 0.96 |
| rs9300549 | 0.42 | 0.38 | 0.2705 | 0.0004 | 37 | G | 0.38 | 0.37 | 0.2793 | 1.06 |
| rs4773194 | 0.18 | 0.17 | 0.8332 | 0.0025 | 161 | A | 0.17 | 0.18 | 0.3968 | 0.94 |
| rs7999702 | 0.17 | 0.2 | 0.2647 | 0.0033 | 200 | G | 0.21 | 0.21 | 0.9617 | 1 |
| rs914009 | 0.33 | 0.31 | 0.6322 | 0.0003 | 24 | T | 0.35 | 0.35 | 0.7209 | 0.98 |
| rs2921452 | 0.46 | 0.45 | 0.7772 | 0.003 | 184 | G | 0.49 | 0.49 | 0.9825 | 1 |
| rs12438353 | 0.29 | 0.33 | 0.2103 | 0.0017 | 116 | T | 0.35 | 0.34 | 0.3369 | 1.06 |
| rs11247363 | 0.41 | 0.45 | 0.3095 | 0.0002 | 19 | T | 0.48 | 0.48 | 0.778 | 1.02 |
| rs4054823 | 0.43 | 0.44 | 0.7791 | 0.001 | 81 | C | 0.44 | 0.47 | 0.04422 | 0.9 |
| rs972317 | 0.15 | 0.11 | 0.1038 | 0.0028 | 175 | G | 0.11 | 0.11 | 0.8008 | 1.02 |
| rs12150382 | 0.21 | 0.26 | 0.1093 | 3E−05 | 4 | A | 0.24 | 0.24 | 0.8583 | 0.99 |
| rs1790588 | 0.54 | 0.51 | 0.447 | 0.0004 | 35 | G | 0.47 | 0.48 | 0.2156 | 0.94 |
| rs2306199 | 0.38 | 0.41 | 0.4524 | 0.0004 | 32 | G | 0.35 | 0.36 | 0.3041 | 0.94 |
| rs2288888 | 0.35 | 0.31 | 0.2413 | 1E−05 | 2 | G | 0.31 | 0.31 | 0.806 | 0.99 |
| rs5992590 | 0.24 | 0.31 | 0.0433 | 0.0005 | 42. | C | 0.26 | 0.26 | 0.9281 | 1.01 |
| rs2091051 | 0.38 | 0.4 | 0.5567 | 0.0019 | 130 | A | 0.46 | 0.47 | 0.3894 | 0.95 |
| rs6010061 | 0.43 | 0.39 | 0.2309 | 0.0005 | 44 | T | 0.47 | 0.46 | 0.5013 | 1.04 |

TABLE 8

Confirmation of SNPs Associated With Aggressiveness of Prostate Cancer in CAPS

| dbSNP ID | Chromosome | Physical Position (bp) | Allele | CGEMS, 1st stage | | | CGESM, 2nd stage | | | | | |
|---|---|---|---|---|---|---|---|---|---|---|---|---|
| | | | | Aggressive-PLCO, n = 691 | indolent-PLCO, n = 489 | P-PLCO | Aggressive-ACS, n = 926 | indolent-ACS, n = 699 | P-ACS | Aggressive-ATBC, n = 240 | indolent-ATBC, n = 516 | P-ATBC |
| rs9996597 | 4 | 111,652 | T | 0.49 | 0.45 | 0.05 | 0.46 | 0.41 | 0.00 | 0.56 | 0.54 | 0.57 |
| rs886505 | 7 | 8,559,297 | A | 0.43 | 0.5 | 4.5E−04 | 0.46 | 0.49 | 0.08 | 0.56 | 0.61 | 0.12 |
| rs2713328 | 7 | 9,260,649 | A | 0.18 | 0.13 | 6.3E−04 | 0.17 | 0.14 | 0.01 | 0.22 | 0.2 | 0.39 |
| rs10217763 | 9 | 22,588,914 | A | 0.19 | 0.22 | 0.03 | 0.19 | 0.23 | 0.03 | 0.17 | 0.2 | 0.17 |
| rs1320722 | 11 | 79,156,374 | T | 0.36 | 0.41 | 0.01 | 0.35 | 0.39 | 0.03 | 0.44 | 0.44 | 0.95 |
| rs4054823 | 17 | 13,565,749 | T | 0.42 | 0.48 | 3.7E−03 | 0.44 | 0.48 | 0.05 | 0.47 | 0.49 | 0.39 |

| dbSNP ID | CGESM, 2nd stage | | | CGEMS | | | CAPS | | | JHH* | | |
|---|---|---|---|---|---|---|---|---|---|---|---|---|
| | Aggressive-HPFS, n = 123 | indolent-HTFS, n = 405 | P-HPFS | P-CMH | Rank | Allele | Aggressive, n = 1,231 | indolent, n = 1,619 | P | Aggressive, n = 1,258 | indolent, n = 4,258 | P |
| rs9996597 | 0.46 | 0.42 | 0.28 | 0.0005 | 41 | T | 0.47 | 0.51 | 0.02 | 0.58 | 0.54 | 0.04 |
| rs886505 | 0.48 | 0.48 | 0.96 | 1.6E−04 | 18 | G | 0.44 | 0.48 | 1.7E−03 | 0.48 | 0.49 | 0.63 |
| rs2713328 | 0.15 | 0.14 | 0.84 | 9E−05 | 9 | C | 0.2 | 0.16 | 2.1E−03 | 0.17 | 0.17 | 0.99 |
| rs10217763 | 0.21 | 0.21 | 0.82 | 1.1E−03 | 90 | G | 0.2 | 0.22 | 0.04 | 0.2 | 0.21 | 0.42 |
| rs1320722 | 0.35 | 0.37 | 0.46 | 2.4E−03 | 156 | C | 0.41 | 0.44 | 0.03 | 0.36 | 0.38 | 0.24 |
| rs4054823 | 0.43 | 0.44 | 0.78 | 9.8E−04 | 81 | C | 0.44 | 0.47 | 0.04 | 0.44 | 0.46 | 0.05 |

*For rs4054823, the numbers of aggressive and indolent subjects are 1408 and 4318, respectively.

That which is claimed is:

1. A method of measuring a prostate specific antigen (PSA) level in a subject, comprising measuring the PSA level in a sample obtained from the subject identified as having the T allele of single nucleotide polymorphism rs4054823.

2. A method of measuring a prostate specific antigen (PSA) level in a subject, comprising:

a) obtaining a nucleic acid sample from the subject;

b) detecting the T allele of single nucleotide polymorphism rs4054823 in the nucleic acid sample by an amplification reaction, an amplification reaction with a single base extension, matrix-assisted laser desorption/ionization-time of flight mass spectrometry (MALDI-TOF-MS), sequencing, hybridization, restriction endonuclease digestion analysis, electrophoresis, or any combination thereof; and c) measuring the PSA level in said subject.

* * * * *

UNITED STATES PATENT AND TRADEMARK OFFICE
CERTIFICATE OF CORRECTION

PATENT NO. : 9,534,256 B2
APPLICATION NO. : 13/344907
DATED : January 3, 2017
INVENTOR(S) : Xu et al.

It is certified that error appears in the above-identified patent and that said Letters Patent is hereby corrected as shown below:

In the Specification

Column 1, Lines 14-19: Please delete the paragraph below the STATEMENT OF GOVERNMENT SUPPORT and insert the following:
--This invention was made with government support under CA106523, CA129684, CA105055, CA095052, and PC051264 awarded by the National Institutes of Health. The government has certain rights in the invention.--

Signed and Sealed this
Ninth Day of May, 2023

Katherine Kelly Vidal
*Director of the United States Patent and Trademark Office*